(12) United States Patent
Beaty

(10) Patent No.: US 12,345,672 B2
(45) Date of Patent: Jul. 1, 2025

(54) METHODS OF CORRECTING FOR UNCOMPENSATED RESISTANCES IN THE CONDUCTIVE ELEMENTS OF BIOSENSORS, AS WELL AS DEVICES AND SYSTEMS INCORPORATING THE SAME

(71) Applicant: Roche Diabetes Care, Inc., Indianapolis, IN (US)

(72) Inventor: Terry A. Beaty, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 1195 days.

(21) Appl. No.: 16/388,623

(22) Filed: Apr. 18, 2019

(65) Prior Publication Data

US 2020/0025707 A1    Jan. 23, 2020

Related U.S. Application Data

(63) Continuation of application No. PCT/US2017/049800, filed on Sep. 1, 2017.
(Continued)

(51) Int. Cl.
*G01N 27/327* (2006.01)
*A61B 5/145* (2006.01)
(Continued)

(52) U.S. Cl.
CPC ..... *G01N 27/3274* (2013.01); *A61B 5/14532* (2013.01); *G01N 27/028* (2013.01); *G01N 33/49* (2013.01)

(58) Field of Classification Search
CPC .......... G01N 27/3274; G01N 27/028
See application file for complete search history.

(56) References Cited

U.S. PATENT DOCUMENTS 4,008,448 A    2/1977  Muggli
4,225,410 A    9/1980  Pace
(Continued)

FOREIGN PATENT DOCUMENTS

JP    2014521943 A    8/2014
WO    2013017218 A1    2/2013
(Continued)

OTHER PUBLICATIONS

Myland et al., Uncompensated Resistance. 1. The Effect of Cell Geometry, Analytical Chemistry, Oct. 2000, 3972-3980, 72.
(Continued)

*Primary Examiner* — C. Sun
(74) *Attorney, Agent, or Firm* — MASCHOFF BRENNAN

(57) ABSTRACT

Methods are provided for correcting for effects of uncompensated resistances in conductive elements of biosensors during electrochemical analyte measurements, where such methods include theoretically segmenting areas of conductive elements of biosensors into a number of conductive "squares," respectively, and using this information to calculate or determine sheet resistance of a biosensor's conductive elements in Ω/square at a time of use by measuring resistance of one or more paths or patterns of the conductive elements and then dividing by a theoretical number of uncompensated conductive squares in the path or pattern of conductive elements to obtain one or more uncompensated resistance values. Measurement errors can be compensated, corrected and/or minimized by subtracting uncompensated resistances from a real portion of a measured impedance.

30 Claims, 11 Drawing Sheets

Related U.S. Application Data

(60) Provisional application No. 62/411,727, filed on Oct. 24, 2016.

(51) Int. Cl.
    *G01N 27/02*      (2006.01)
    *G01N 33/49*      (2006.01)

(56) References Cited

U.S. PATENT DOCUMENTS

| | | |
|---|---|---|
| 4,233,029 A | 11/1980 | Columbus |
| 4,323,536 A | 4/1982 | Columbus |
| 4,720,372 A | 1/1988 | Fey et al. |
| 4,891,319 A | 1/1990 | Roser |
| 4,919,770 A | 4/1990 | Preidel et al. |
| 4,963,814 A | 10/1990 | Parks et al. |
| 4,999,582 A | 3/1991 | Parks et al. |
| 4,999,632 A | 3/1991 | Parks |
| 5,053,199 A | 10/1991 | Keiser et al. |
| 5,108,564 A | 4/1992 | Szuminsky et al. |
| 5,120,420 A | 6/1992 | Nankai et al. |
| 5,122,244 A | 6/1992 | Hoenes et al. |
| 5,128,015 A | 7/1992 | Szuminsky et al. |
| 5,243,516 A | 9/1993 | White |
| 5,271,895 A | 12/1993 | McCroskey et al. |
| 5,282,950 A | 2/1994 | Dietze et al. |
| 5,288,636 A | 2/1994 | Pollmann et al. |
| 5,352,351 A | 10/1994 | White et al. |
| 5,366,609 A | 11/1994 | White et al. |
| 5,371,687 A | 12/1994 | Holmes, II et al. |
| 5,379,214 A | 1/1995 | Arbuckle et al. |
| 5,385,846 A | 1/1995 | Kuhn et al. |
| 5,405,511 A | 4/1995 | White et al. |
| 5,413,690 A | 5/1995 | Kost et al. |
| 5,437,999 A | 8/1995 | Diebold et al. |
| 5,438,271 A | 8/1995 | White et al. |
| 5,508,171 A | 4/1996 | Walling et al. |
| 5,526,111 A | 6/1996 | Collins et al. |
| 5,594,906 A | 1/1997 | Holmes, II et al. |
| 5,627,075 A | 5/1997 | Bateson |
| 5,628,890 A | 5/1997 | Carter et al. |
| 5,682,884 A | 11/1997 | Hill et al. |
| 5,694,932 A | 12/1997 | Michel |
| 5,727,548 A | 3/1998 | Hill et al. |
| 5,762,770 A | 6/1998 | Pritchard et al. |
| 5,858,691 A | 1/1999 | Hoenes et al. |
| 5,975,153 A | 1/1999 | Hill et al. |
| RE36,268 E | 8/1999 | Szuminsky et al. |
| 5,948,695 A | 9/1999 | Douglas et al. |
| 5,997,817 A | 12/1999 | Crismore et al. |
| 6,001,239 A | 12/1999 | Douglas et al. |
| 6,004,441 A | 12/1999 | Fujiwara et al. |
| 6,025,203 A | 2/2000 | Vetter et al. |
| 6,054,039 A | 4/2000 | Shieh |
| 6,134,504 A | 10/2000 | Douglas et al. |
| 6,144,922 A | 11/2000 | Douglas et al. |
| 6,162,639 A | 12/2000 | Douglas |
| 6,207,000 B1 | 3/2001 | Schwobel et al. |
| 6,245,215 B1 | 6/2001 | Douglas et al. |
| 6,254,736 B1 | 7/2001 | Earl et al. |
| 6,270,637 B1 | 8/2001 | Crismore et al. |
| 6,271,045 B1 | 8/2001 | Douglas et al. |
| 6,319,719 B1 | 11/2001 | Bhullar et al. |
| 6,406,672 B1 | 6/2002 | Bhullar et al. |
| 6,413,213 B1 | 7/2002 | Essenpreis et al. |
| 6,413,395 B1 | 7/2002 | Bhullar et al. |
| 6,425,863 B1 | 7/2002 | Werner et al. |
| 6,428,664 B1 | 8/2002 | Bhullar et al. |
| 6,447,657 B1 | 9/2002 | Bhullar et al. |
| 6,451,264 B1 | 9/2002 | Bhullar et al. |
| 6,455,324 B1 | 9/2002 | Douglas |
| 6,488,828 B1 | 12/2002 | Bhullar et al. |
| 6,506,575 B1 | 1/2003 | Knappe et al. |
| 6,540,890 B1 | 4/2003 | Bhullar et al. |
| 6,562,210 B1 | 5/2003 | Bhullar et al. |
| 6,564,368 B1 | 5/2003 | Beckett et al. |
| 6,582,573 B2 | 6/2003 | Douglas et al. |
| 6,592,815 B1 | 7/2003 | Zimmer |
| 6,627,057 B1 | 9/2003 | Bhullar et al. |
| 6,635,167 B1 | 10/2003 | Batman et al. |
| 6,638,772 B1 | 10/2003 | Douglas et al. |
| 6,645,368 B1 | 11/2003 | Beaty et al. |
| 6,662,439 B1 | 12/2003 | Bhullar |
| 6,755,949 B1 | 6/2004 | Bhullar et al. |
| 6,767,440 B1 | 7/2004 | Bhullar et al. |
| 6,780,296 B1 | 8/2004 | Bhullar et al. |
| 6,780,651 B2 | 8/2004 | Douglas et al. |
| 6,787,109 B2 | 9/2004 | Haar et al. |
| 6,814,843 B1 | 11/2004 | Bhullar et al. |
| 6,814,844 B2 | 11/2004 | Bhullar et al. |
| 6,858,433 B1 | 2/2005 | Zivitz |
| 6,866,758 B2 | 3/2005 | Bhullar et al. |
| 6,927,749 B1 | 8/2005 | Klemm |
| 6,945,955 B1 | 9/2005 | Michel et al. |
| 7,008,799 B1 | 3/2006 | Zimmer et al. |
| 7,018,843 B2 | 3/2006 | Heller |
| 7,018,848 B2 | 3/2006 | Douglas et al. |
| 7,025,836 B1 | 4/2006 | Zimmer et al. |
| 7,045,054 B1 | 5/2006 | Buck et al. |
| 7,063,774 B2 | 6/2006 | Bhullar et al. |
| 7,067,320 B2 | 6/2006 | Klimant |
| 7,073,246 B2 | 7/2006 | Bhullar et al. |
| 7,115,362 B2 | 10/2006 | Douglas et al. |
| 7,192,752 B2 | 3/2007 | Xu et al. |
| 7,208,119 B1 | 4/2007 | Kurtock et al. |
| 7,238,534 B1 | 7/2007 | Zimmer |
| 7,276,146 B2 | 10/2007 | Wilsey |
| 7,276,147 B2 | 10/2007 | Wilsey |
| 7,291,107 B2 | 11/2007 | Hellwig et al. |
| 7,335,286 B2 | 2/2008 | Abel et al. |
| 7,338,639 B2 | 3/2008 | Burke et al. |
| 7,347,973 B2 | 3/2008 | Douglas et al. |
| 7,386,937 B2 | 6/2008 | Bhullar et al. |
| 7,390,667 B2 | 6/2008 | Burke et al. |
| 7,407,811 B2 | 8/2008 | Burke et al. |
| 7,417,811 B2 | 8/2008 | Chang |
| 7,429,865 B2 | 9/2008 | Dreibholz et al. |
| 7,452,457 B2 | 11/2008 | Burke et al. |
| 7,473,398 B2 | 1/2009 | Bhullar et al. |
| 7,476,827 B1 | 1/2009 | Bhullar et al. |
| 7,479,211 B2 | 1/2009 | Bhullar et al. |
| 7,488,601 B2 | 2/2009 | Burke et al. |
| 7,494,816 B2 | 2/2009 | Burke et al. |
| 7,510,643 B2 | 3/2009 | Bhullar et al. |
| 7,540,947 B2 * | 6/2009 | Ueno .................... C12Q 1/001 204/403.01 |
| 7,545,148 B2 | 6/2009 | Lorimer et al. |
| 7,556,723 B2 | 7/2009 | Funke et al. |
| 7,569,126 B2 * | 8/2009 | Celentano .......... G01N 27/327 204/403.01 |
| 7,597,793 B2 | 10/2009 | Burke et al. |
| 7,601,299 B2 | 10/2009 | Beaty et al. |
| 7,638,033 B2 | 12/2009 | Kasielke et al. |
| 7,638,095 B2 | 12/2009 | Sabol |
| 7,727,467 B2 | 6/2010 | Burke et al. |
| 7,731,835 B2 | 6/2010 | Buck et al. |
| 7,751,864 B2 | 7/2010 | Buck, Jr. |
| 7,780,827 B1 | 8/2010 | Bhullar et al. |
| 7,820,451 B2 | 10/2010 | Brauner |
| 7,867,369 B2 | 1/2011 | Bhullar et al. |
| 7,892,849 B2 | 2/2011 | Burke et al. |
| RE42,560 E | 7/2011 | Crismore et al. |
| 7,977,112 B2 | 7/2011 | Burke et al. |
| 7,981,363 B2 | 7/2011 | Burke et al. |
| RE42,924 E | 11/2011 | Crismore et al. |
| RE42,953 E | 11/2011 | Crismore et al. |
| 8,148,164 B2 | 4/2012 | Diebold et al. |
| 8,180,423 B2 | 5/2012 | Mang et al. |
| 8,231,768 B2 | 7/2012 | Ueno et al. |
| 8,298,401 B2 | 10/2012 | Wilsey |
| 8,298,828 B2 | 10/2012 | Diebold et al. |
| 8,329,026 B2 | 12/2012 | Wilsey |
| 8,377,707 B2 | 2/2013 | Burke et al. |
| 8,388,820 B2 | 3/2013 | Ueno et al. |

(56) References Cited

U.S. PATENT DOCUMENTS

| | | |
|---|---|---|
| 8,420,404 B2 | 4/2013 | Diebold et al. |
| 8,431,408 B2 | 4/2013 | Lewis et al. |
| 8,496,794 B2 | 7/2013 | Ueno et al. |
| 8,568,579 B2 | 10/2013 | Ueno et al. |
| 8,574,423 B2 | 11/2013 | Ueno et al. |
| 8,888,974 B2 | 11/2014 | Ueno et al. |
| 8,888,975 B2 | 11/2014 | Ueno et al. |
| 8,900,430 B2 | 12/2014 | Ueno et al. |
| 8,920,628 B2 | 12/2014 | Gerber et al. |
| 9,068,931 B2 | 6/2015 | Ueno et al. |
| 9,074,997 B2 | 7/2015 | Ueno et al. |
| 9,074,998 B2 | 7/2015 | Ueno et al. |
| 9,074,999 B2 | 7/2015 | Ueno et al. |
| 9,075,000 B2 | 7/2015 | Ueno et al. |
| 9,080,954 B2 | 7/2015 | Ueno et al. |
| 9,080,955 B2 | 7/2015 | Ueno et al. |
| 9,080,956 B2 | 7/2015 | Ueno et al. |
| 9,080,957 B2 | 7/2015 | Ueno et al. |
| 9,080,958 B2 | 7/2015 | Ueno et al. |
| 9,080,960 B2 | 7/2015 | Ueno et al. |
| 9,086,372 B2 | 7/2015 | Ueno et al. |
| 2003/0031592 A1 | 2/2003 | Knappe |
| 2006/0003397 A1 | 1/2006 | Knappe et al. |
| 2009/0093979 A1 | 4/2009 | Hyland et al. |
| 2009/0223817 A1 | 9/2009 | Ueno et al. |
| 2015/0076010 A1* | 3/2015 | Austera ............. G01N 27/3272 205/792 |
| 2015/0362455 A1 | 12/2015 | Moore et al. |

FOREIGN PATENT DOCUMENTS

| | | |
|---|---|---|
| WO | 2014037372 A1 | 3/2014 |
| WO | 2014068022 A1 | 5/2014 |
| WO | 2014068024 A1 | 5/2014 |
| WO | 2014140164 A1 | 9/2014 |
| WO | 2014140170 A1 | 9/2014 |
| WO | 2014140172 A1 | 9/2014 |
| WO | 2014140173 A1 | 9/2014 |
| WO | 2014140177 A2 | 9/2014 |
| WO | 2014140718 A2 | 9/2014 |
| WO | 2015187580 A1 | 12/2015 |
| WO | 2017039976 A1 | 3/2017 |

OTHER PUBLICATIONS

Office Action mailed on Jul. 28, 2020 in JP Application No. 2019-521805; 4 pages.

International Search Report and Written Opinion mailed Nov. 16, 2019 in International Application No. PCT/US2017/049800.

Berger, "Contact Resistance and Contact Resistivity", Journal of the Electrochemical Society, vol. 119, No. 4, Apr. 30, 1972 (Apr. 30, 1972), p. 507-514.

* cited by examiner

METHODS OF CORRECTING FOR UNCOMPENSATED RESISTANCES IN THE CONDUCTIVE ELEMENTS OF BIOSENSORS, AS WELL AS DEVICES AND SYSTEMS INCORPORATING THE SAME

CROSS-REFERENCE TO RELATED APPLICATIONS

This patent application claims priority to and the benefit of U.S. Provisional Patent Application No. 62/411,727 (filed 24 Oct. 2016), and is a continuation of International Patent Application No. PCT/US2017/049800 (filed 1 Sep. 2017). The contents of these applications are incorporated herein by reference in their entirety.

TECHNICAL FIELD

The disclosure relates generally to mathematics and medicine/medical diagnostics, and more particularly, it relates to correcting, compensating, and/or minimizing the effects of uncompensated resistances that may be present in the conductive elements of biosensors used for electrochemically measuring an analyte in a body fluid sample.

BACKGROUND

Devices, systems, and methods for assaying analytes in body fluids, as well as biosensors for use therein, are well known. For example, electrochemical-based measuring methods are known that generally rely upon correlating a current (amperometry), a potential (potentiometry), or an accumulated charge (coulometry) to an analyte concentration, typically in conjunction with a detection reagent that produces charged-carriers when combined with an analyte of interest. Biosensors for conducting such electrochemical tests typically are disposable test elements such as test strips.

In general, biosensors have a reaction zone that includes measurement electrodes in communication with one or more detection reagents that come into direct contact and thus chemically interact with a body fluid sample. In some amperometric and coulometric electrochemical-based measurement systems, the measurement electrodes are attached to electronic circuitry in a test meter that supplies an electrical potential to the measurement electrodes and measures a response of the biosensor to this potential (e.g., current, impedance, charge, etc.). As such, the biosensor is attached/inserted into the test meter, which then measures a reaction between an analyte in the body fluid sample and the detection reagent to determine the analyte concentration, where the measured response is proportional to the analyte concentration.

For biosensors in which the electrodes, conductive traces, contact pads/terminals and any other conductive elements are made from electrically conductive thin films (e.g., carbon ink, conductive polymers, metals, noble metals, silver paste and hybrids thereof, etc.), the resistance of the conductive traces that connect the reaction zone to the electronic circuitry in the test meter can measure several hundred ohms (0) or more. This resistance causes a potential drop along the length of the traces so that the potential presented to the measurement electrodes in the reaction zone is less than the potential applied by the test meter to contact pads of the biosensor.

The potential drop from a point of contact between the electronic circuitry in the test meter and contact pads for the WE and CE to a point close to the respective WE and CE in the reaction zone can be compensated by having the electronic circuit apply an increased voltage to achieve the desired voltage at the reaction zone, thereby compensating for any IR drop through the conductive elements. See, e.g., U.S. Pat. No. 7,569,126. This can be done less precisely empirically assuming sheet resistance ($R_s$) is reasonably controlled or can be done more precisely and dynamically by using Kelvin (or voltage-sensing) connections. Unfortunately, small regions remain uncompensated for in the WE and/or CE because they are beyond the compensation regions or loops of the test system (i.e., uncompensated resistance or $R_{UNC}$).

For example, FIG. 1 shows a conventional two-electrode electrochemical biosensor 100 connected to a generic measurement device 102 such as a test meter. The measurement device 102 includes a measuring circuit 102a. When a voltage is applied by the measurement device 102, an electrochemical reaction can take place in the presence of a sample having an analyte of interest. A subsequent current value generated by the presence of the analyte then can be detected by the measurement device 102 and can be analyzed to determine an analyte concentration in the sample. More specifically, the measurement device 102 can apply a potential difference of $V_1$ between the biosensor's contact with working electrode (WE) trace 110 and counter electrode (CE) trace 108 and measure a generated loop current ($I_{LOOP}$). The measurement device 102 further can compute impedance (Z) of a load or a cell by $V_1/I_{LOOP}$. In some instances, impedances for a WE trace 110 and/or a CE trace 108 can impact the overall impedance calculations. If the current and trace resistances are small, however, the current×resistance (I×R) losses associated with the biosensor 100 connections and traces remain small. In this instance of low resistance connecting traces, the potential at the load, $V_2$, will be approximately equal to $V_1$, and the computation accuracy is unaffected by I×R losses.

In some biosensors, $I_{LOOP}$ can be kept small by reducing $|V_1|$ or by increasing the load impedance. The latter, however, is not within the measurement device's control since it is determined as a property of the biosensor's design and as properties of a sample (e.g., a biosensor with a lower loop resistance). Trace resistance on a planar substrate can be kept small by using highly conductive (i.e., metallic) materials, by keeping the traces wide, and/or by keeping the traces thick. Unfortunately, these three attributes can be difficult to maintain in small, inexpensive, single-use biosensors, as miniaturization pushes toward reduced trace widths, and cost pressures push towards less expensive conductive materials of minimal thickness.

As noted above, Kelvin connections have been known and used as an electrical impedance measurement technique. Such a measurement technique employs separate pairs of current-carrying traces and voltage-sensing (or reference) traces to enable more accurate measurements of unknown load impedances (i.e., four-terminal sensing). Adding one or more remotely connected voltage-sensing traces to one or more electrodes allows an excitation circuit to detect the potential available at or near the load. This arrangement allows the measuring circuit to adjust $V_1$ to compensate for I×R losses in current-carrying paths of conductive elements and connections between the voltage source and load. A measuring circuit's excitation can be configured to dynamically adjust $V_1$ potential over a wide range of trace and load resistances based on a difference between desired and sensed potentials.

For example, FIGS. 2-3 show a conventional two-electrode electrochemical biosensor 200 having a sample receiving chamber 114, where the biosensor 200 is connected to a generic measurement device 102 such as a test meter. When compared to the biosensor 100 of FIG. 1, the biosensor 200 includes one Kelvin connection in the form of a WE voltage-sensing trace 112 in electrical communication with an end of the WE 104. By this configuration, the measuring circuit can compensate for I×R losses along the WE trace 110 by increasing the excitation to $V_1'=V_1+I\times R$, forcing $V_2$ closer to the desired $V_1$. By using the WE voltage-sensing trace 112, the biosensor's conductive elements can be made narrower by decreasing, for example, the WE trace 110 width. Likewise, by using the WE voltage-sensing trace 112, the biosensor 200 may be made less expensive by reducing the WE trace 110 thickness or by making the WE trace 110 from a more resistive material. I×R losses along the CE trace 108 will have the same impact on $V_2$ error as in FIG. 1. A measuring circuit sense input should have a high input impedance, ideally limiting the WE sense trace 112 current to 0 nA. Additional voltage-sensing traces also can be used. See, e.g., FIG. 4; as well as U.S. Pat. Nos. 7,540,947; 7,556,723; 7,569,126; 8,231,768; 8,388,820; 8,496,794; 8,568,579; 8,574,423; 8,888,974; 8,888,975; 8,900,430; 9,068,931; 9,074,997; 9,074,998; 9,074,999; 9,075,000; 9,080,954; 9,080,955; 9,080,956; 9,080,957; 9,080,958; 9,080,960 and 9,086,372.

Voltage-sensing traces, however, have limits. For example, physical, economic or practical considerations may restrict where voltage-sensing traces are connected to a biosensor's conductive elements, and therefore how accurately these leads represent the true operating potential at the active load. Moreover, additional (e.g., uncompensated) trace resistance 'after' or 'outside' any voltage-sensing trace connections may become a significant source of load impedance calculation error as the measured current increases, the load impedance decreases or the trace resistance increases or varies.

Accordingly, a need exists for improved methods of compensating, correcting and/or minimizing the effects of uncompensated resistance ($R_{UNC}$) that may be present in the conductive elements of biosensors used for electrochemically analyzing an analyte in a body fluid sample to thereby increase biosensor computational accuracy and reliability.

BRIEF SUMMARY

This disclosure is directed toward improving electrochemical analyte measurement accuracy and reliability of analyte measurement systems in view of $R_{UNC}$ that may be present in biosensors having conductive elements with low conductivity or having conductive elements with highly variable sheet resistances. An inventive concept herein is achieved by segmenting areas of the conductive elements (e.g., CE and WE) of biosensors into a theoretical number of conductive "squares," respectively, and using this information to calculate or determine $R_s$ of a biosensor in Ω/square at a time of use by measuring resistance of one or more paths or patterns of the conductive elements and dividing by the theoretical number of conductive squares in that path or pattern of conductive elements (i.e., one or more compensation loops formed by voltage-sensing traces). A value for $R_{UNC}$ is then obtained by multiplying $R_s$ by a number of theoretical, uncompensated conductive squares 'after,' 'beyond' or 'outside' that pattern or path of conductive elements used to determine $R_s$. Measurement errors can be compensated, corrected and/or minimized by subtracting $R_{UNC}$ from a real portion of a measured impedance. This inventive concept can be incorporated into exemplary devices, systems and methods as described herein and in more detail below.

For example, methods are provided for compensating, correcting and/or minimizing effects of $R_{UNC}$ in the conductive elements of biosensors during electrochemical analyte measurements. Such methods include providing a biosensor having one or more conductive elements, where such conductive elements can be one of more of a WE, a WE trace, a WE contact pad, a WE voltage-sensing trace, a WE voltage-sensing contact pad, a CE, a CE trace, a CE contact pad, a CE voltage-sensing trace, and a CE voltage-sensing contact pad.

The methods also include applying or providing a potential to the conductive elements and then measuring resistance of at least one structure of the conductive elements with at least two contacts. In some instances, the resistance is a resistance of at least one compensation loop that includes a voltage-sensing trace.

In some instances, the applied or provided potential includes one or more alternating current (AC) components. In certain instances, the one or more AC components include at least a 20 kHz segment. In particular instances, the one or more AC components include a sequence of a first 10 kHz segment, a 20 kHz segment, a second 10 kHz segment, a 2 kHz segment, and a 1 kHz segment. In other instances, the applied or provided potential further includes one or more direct current (DC) components.

The methods also include determining $R_s$ for one or more compensation loops present in the conductive elements, where the one or more compensation loops include a voltage-sensing connection. In some instances, $R_s$ can be calculated by measuring resistance of the one or more compensation loops and dividing the measured loop resistance by a number of conductive squares therein.

The methods also include determining $R_{UNC}$ for resistance(s) 'after,' 'beyond' or 'outside' voltage-sensing trace connections to the conductive elements of such biosensors. In some instances, $R_{UNC}$ can be calculated by multiplying $R_s$ by a number of uncompensated conductive squares present in the path or pattern of conductive elements 'after,' 'beyond' or 'outside' any voltage-sensing trace connections (i.e., after, beyond or outside the compensation loop).

The methods also include adjusting, compensating and/or minimizing effects of the $R_{UNC}$ by subtracting $R_{UNC}$ from a real portion of a measured impedance.

The methods also include determining a concentration of an analyte of interest in view of the adjusted, compensated and/or minimized $R_{UNC}$.

In view of the above, devices and systems also are provided for correcting for uncompensated resistances during electrochemical analyte measurements. Such devices can be a test meter having at least a programmable processor associated with a controller/microcontroller that is connected with memory and associated test signal generating and measuring circuitry that are operable to generate a test signal, to apply the signal to a biosensor, and to measure one or more responses of the biosensor to the test signal, where the test meter is configured to execute the methods as described herein.

Such systems can include the test meter as described herein and at least one biosensor for use therein.

The devices, systems and methods described herein therefore find use in monitoring and treating diseases and disorders, as well as find use in adjusting a treatment for a disease or disorder.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Corresponding reference characters indicate corresponding parts throughout the several views of the drawings.

Figure 1:
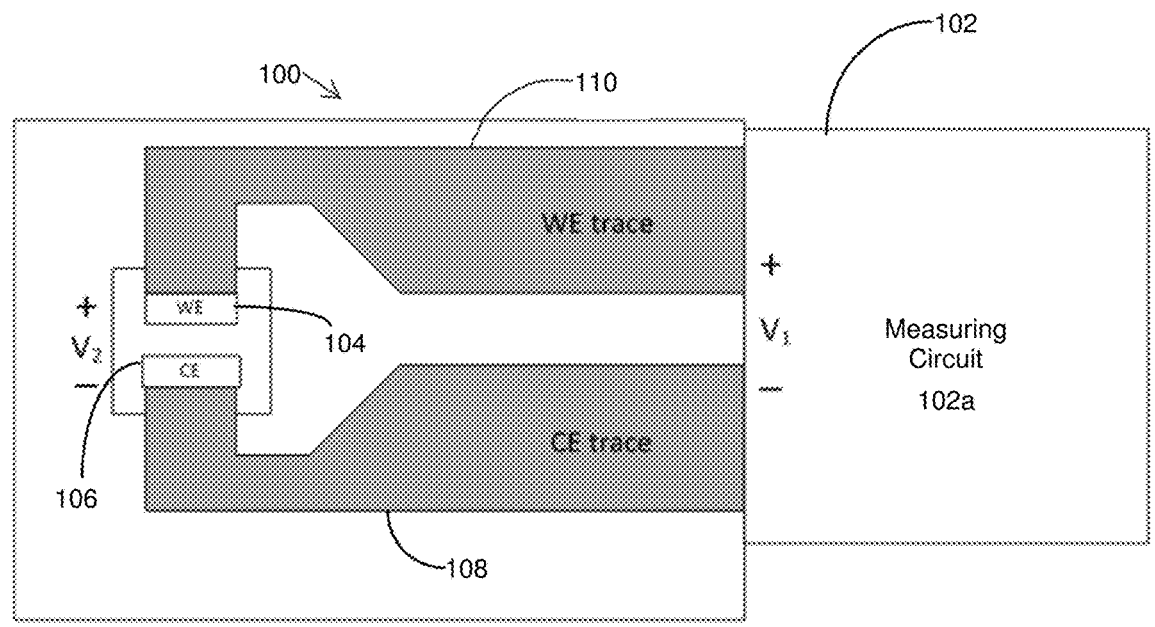
FIG. 1. is a simplified schematic view of a prior art two-electrode electrochemical biosensor.
Figure 2:
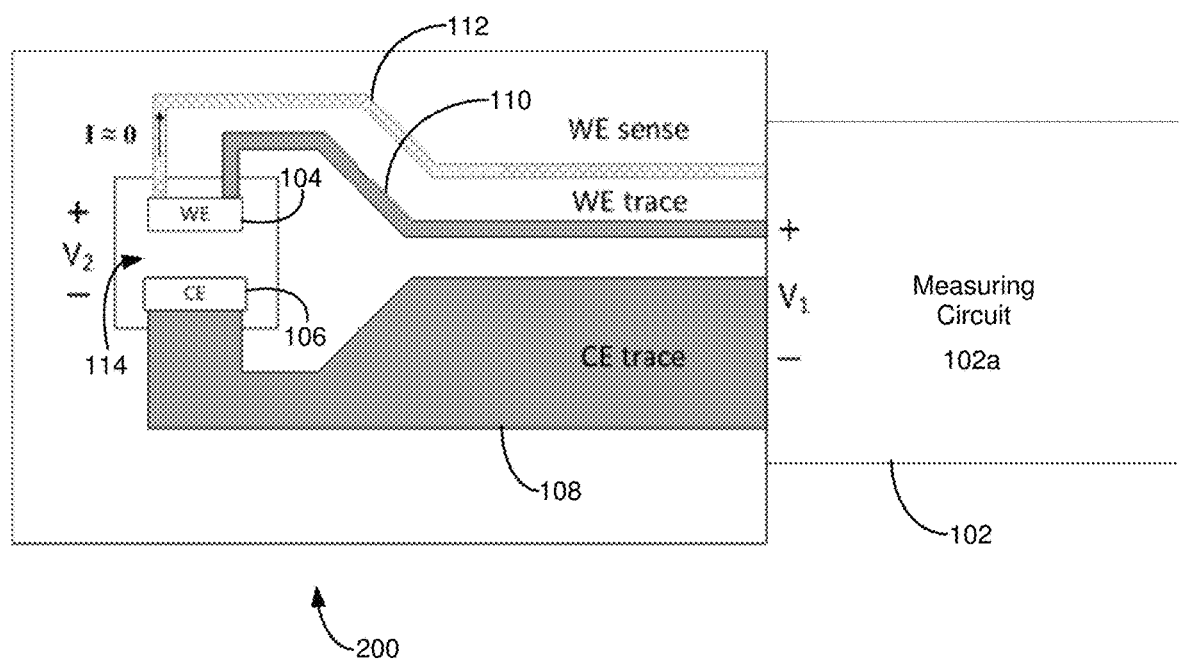
FIG. 2 is a simplified schematic view of a prior art two-electrode electrochemical biosensor having a single Kelvin sense connection.
Figure 3:
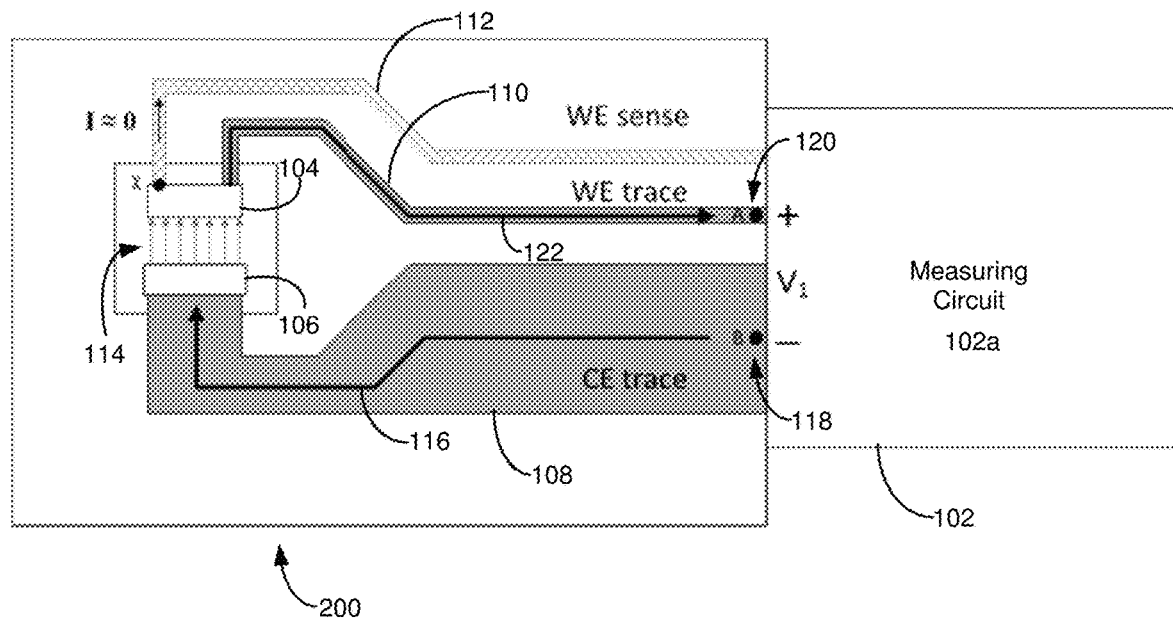
FIG. 3 is a schematic view of the two-electrode electrochemical biosensor of FIG. 2 during an electrochemical measurement.
Figure 4:
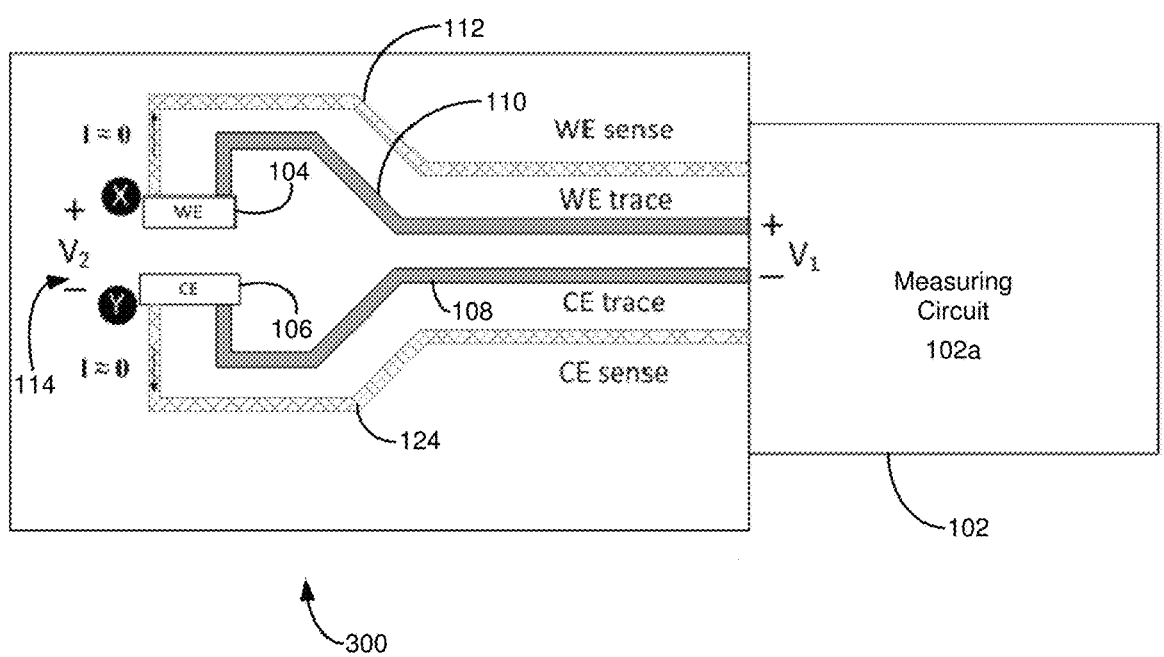
FIG. 4 is a simplified schematic view of a two-electrode electrochemical biosensor having a plurality of Kelvin sense connections.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The devices, systems and methods now will be described more fully hereinafter with reference to the accompanying drawings, in which some, but not all embodiments of the inventive concept are shown. Indeed, the devices, systems and methods may be embodied in many different forms and should not be construed as limited to the embodiments set forth herein; rather, these embodiments are provided so that this disclosure will satisfy applicable legal requirements.

Likewise, many modifications and other embodiments of the devices, systems and methods described herein will come to mind to one of skill in the art to which the disclosure pertains having the benefit of the teachings presented in the foregoing descriptions and the associated drawings. Therefore, it is to be understood that the devices, systems and methods are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Overview

This disclosure is directed toward compensating, correcting and/or minimizing for effects of $R_{UNC}$ that often is present in the conductive elements of biosensors for electrochemical analyte measurement systems. By using precise and known electrode geometry and design of an electrode system, overall $R_s$ and then $R_{UNC}$ of an interrogated biosensor can be determined and used mathematically to correct for error of the measured current and impedance values that arise from the uncompensated regions to provide a more accurate and reliable analyte concentration.

Figure 7:
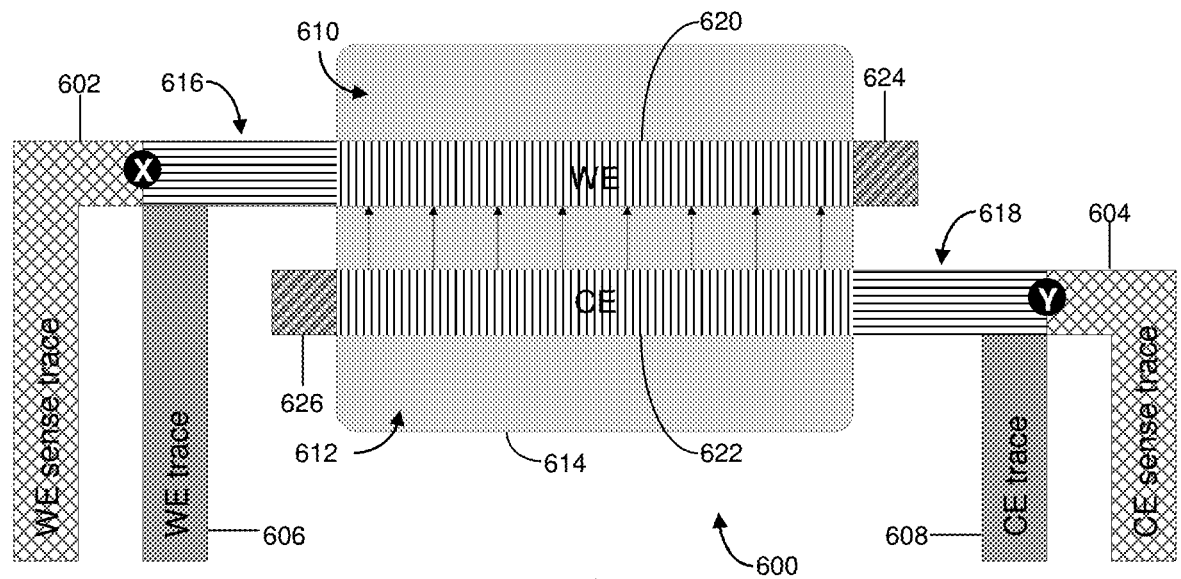
FIG. 7 is a simplified diagram of a coplanar, two-electrode biosensor with compensated Kelvin connections in accordance with the present disclosure.
Figure 9:
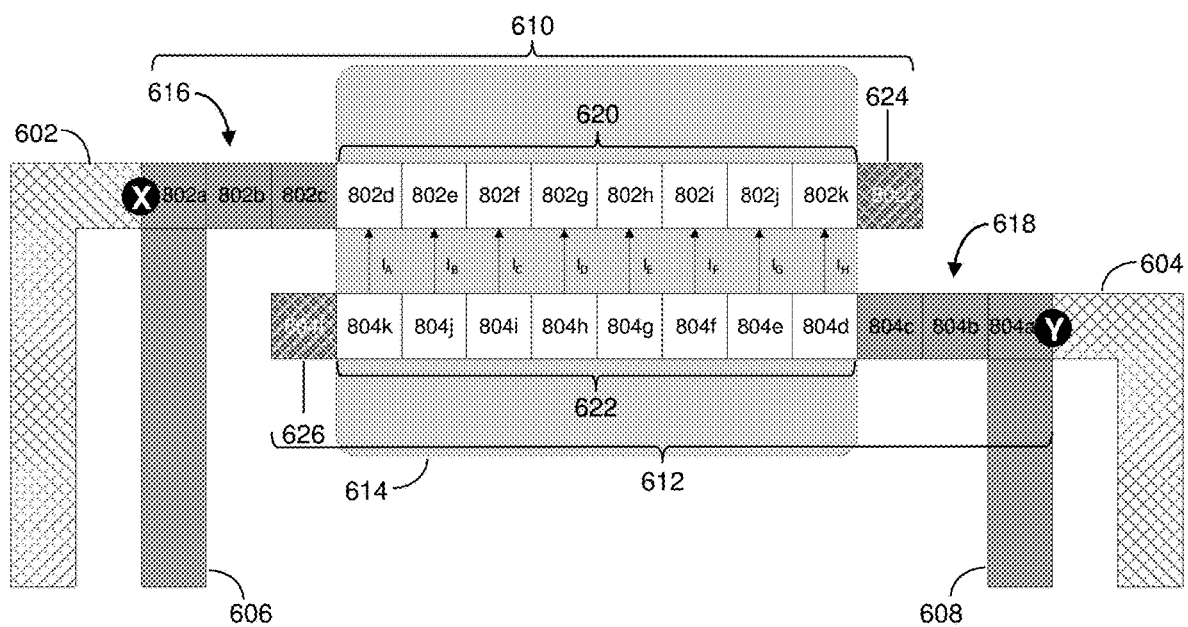
FIG. 9 is a simplified diagram of the two-electrode biosensor of FIG. 7 illustrating the WE and CE segmented into conductive squares.

In this manner, careful electrode cell design and trace connections can reduce the amount of $R_{UNC}$ that can be present 'after,' 'beyond' or 'outside' Kelvin (i.e., voltage-sensing trace) connections in the conductive elements of biosensors and can minimize the active potential error. $R_{UNC}$, however, cannot be entirely eliminated through careful electrode cell design. Thus, for example, portions 616, 620, 624 and 618, 622 and 626 of FIGS. 7 and 9 represent areas of the conductive elements considered 'after,' 'beyond' or 'outside' points X and Y that contribute to $R_{UNC}$. Moreover, an ideal biosensor design can be restricted by system requirements, physical size, cost constraints, and even design complexity. Likewise, the $R_s$ of printed or sputtered conductive films is difficult to precisely control and may vary from lot to lot. As such, for a given electrode geometry, resistance changes in small uncompensated regions can influence impedance measurements in electrochemical-based analyte detections.

Moreover, $R_s$ can vary based on the material used and on the thickness of the material applied to the substrate. In electrochemical biosensors, gold is used as a trace material, which can be applied to a substrate using a metal sputtering process. In some instances, gold can be used alone as a trace material such as, for example, a 500 Å gold layer. At this thickness, the gold layer can have a sensitivity to thickness and sputtering time of approximately −0.032 (Ω/sq)/nm. Further reducing the thickness to, for example, 100 Å can make the trace more sensitive to variations in thickness and sputtering time (e.g., −0.8 (Ω/sq)/nm). Thus, it can be seen that using a thicker material can allow for less variation in resistance across the trace, making estimations of the given resistance per/square less sensitive to these variations.

Alternatively, hybrid materials can be used to provide suitable variations in impedance while reducing material cost. One such hybrid material is a gold/palladium composite. In one example, a 100 Å gold layer can be deposited over a 300 Å layer of palladium. This hybrid material generally has a $R_s$ of 4.2 Ω/square, whereas a 500 Å layer of gold generally has a $R_s$ of 1.59 Ω/square. Further, a gold/palladium hybrid trace material can exhibit a linear increase in resistance with increasing temperature. For example, for the 100 Å gold layer over the 300 Å palladium layer, the resistance increase can average about +4.22 Ω/square/° C.

Advantageously, broad field laser ablation can produce biosensors having planar conductive elements in thin metal layers with reasonable accuracy and precision. Herein, the dimensional precision is sufficient to allow one to determine $R_s$ of one or more conductive elements of a biosensor in Ω/square at time of use by measuring the resistance of one or more selected areas in the conductive elements, such as a compensation loop (i.e., CE contact pad, CE trace, CE voltage-sensing trace and CE voltage-sensing contact pad and/or WE contact pad, WE trace, WE voltage-sensing trace and WE voltage-sensing contact pad) and dividing by a theoretical number of conductive 'squares' therein. As used herein, "sheet resistance" or "$R_s$" means a concept that applies to uniform conductive layers sufficiently thin to be considered two dimensional (length (L) and width (W); as thickness (T)<<L and W).

Theoretically, resistance (R) of such a conductive layer/sheet can be approximated as R (Ω)=$R_s$×(L/W), where the units of L/W cancel and thus imply a square unit of area. Experimentally, however, one can measure one or more loop resistances on the biosensor and then calculate $R_s$, which also accounts for an actual temperature at the time of measurement. $R_{UNC}$ then can be predicted by multiplying $R_s$ by the theoretical number of uncompensated conductive squares in the conductive path of the biosensor that is 'after,' 'beyond' or 'outside' the voltage-sensing trace connections to the CE and/or WE, respectively, as shown below in Equation 1.

As used herein, "conductive square" or "conductive squares" mean a theoretically designated or defined area in the conductive elements of a biosensor, which is a unitless measure of an aspect ratio of a conductive path in the conductive elements, broken down into the number of squares (based on the width) that can be experimentally or theoretically determined in uncompensated and active portions of the conductive path. In one sense, the effective surface area of the conductive path is approximated as a number of squares. One of skill in the art understands that the number of squares in the conductive elements can be an even number or an odd number of squares and also can include fractions. The number of squares, however, will be limited by the overall geometry of the conductive elements as it is based upon the area (e.g., L×W for rectangular geometries) thereof.

Herein, the number of conductive squares in the biosensor's conductive elements (i.e., CE and WE geometry) may be estimated, calculated or determined experimentally. In this manner, the biosensor's $R_{UNC}$ may be roughly estimated as:

$$R_{UNC} = Rs\left(\frac{\Omega}{\text{square}}\right) \times N(\text{total uncompensated conductive squares}) \quad \text{Equation 1}$$

The $R_{UNC}$ then may be subtracted from a real portion of a relevant impedance (Z) measurement and may be used to correct a measured impedance calculation to minimize inaccuracies due to the value or variations in the conductive elements' $R_s$ (e.g., $Z'_{REAL}$ (Ω)=$Z_{REAL}$ (Ω)−$R_{UNC}$).

As used herein, "parasitic resistance" is unintentional additional resistance responsible for a potential (i.e., voltage) drop that is undesirable along a length of the conductive elements (e.g., electrodes, traces, and contact pads, etc.) of a biosensor. Consequently, the potential presented to the measurement electrodes (e.g., CE and WE) in a reaction zone is notably less than the potential applied across contact pads of the biosensor by a measurement device such as a test meter. In many cases, parasitic resistance can be compensated within a biosensor design by using voltage-sensing connections that can be used to dynamically adjust the applied potential of the measurement device to achieve the desired potential at the point of the sensing connection. Likewise, and as used herein, "uncompensated resistance" or "$R_{UNC}$" means a parasitic resistance that is not corrected by means of voltage-sensing connections. Because the impedance of the reaction taking place within the reaction zone can be within an order of magnitude of the $R_{UNC}$ of the biosensor, a signal being measured can have a significant offset due to the I×R drop induced by the $R_{UNC}$. If this offset varies from biosensor to biosensor, then noise or error will be included in the measurement results.

To manipulate resistance along any conductive path, one may alter the length or width thereof (thus changing the number of "squares") or one may alter the thickness or material of a conductive layer (thus changing the $R_s$) to increase or decrease a predicted resistance value for that particular conductive path to fall within a desired range of resistance values. Determining the number of squares for a particular conductive path in a variety of patterns and configurations other than generally straight line paths is within the ordinary skill in the art and requires no further explanation here.

Advantageously, the test systems and methods herein can be used to implement a variety of calibrations, compensations, or corrections that can be tailored to a specific biosensor or test system and the operational parameters for the system to improve an electrochemical measurement's accuracy and reliability.

Systems Including Measurement Devices and Biosensors

Test systems herein can include a measurement device and one or more biosensors. Although the methods described herein may be used with measurement devices and biosensors having a wide variety of designs and made with a wide variety of manufacturing processes and techniques, an exemplary test system including a measurement device 102 such as a test meter operatively coupled with an electrochemical biosensor 100 is shown in FIG. 5.

Typically, the measurement device 102 and the biosensor 100 are operable to determine concentrations of one or more analytes of interest in a sample provided to the biosensor 100. In some instances, the sample may be a body fluid sample such as, for example, whole blood, plasma, saliva, serum, sweat, or urine. In other instances, the sample may be another type of fluid sample to be tested for the presence or concentration of one or more electrochemically reactive analyte(s) such as an aqueous environmental sample.

Figure 5:
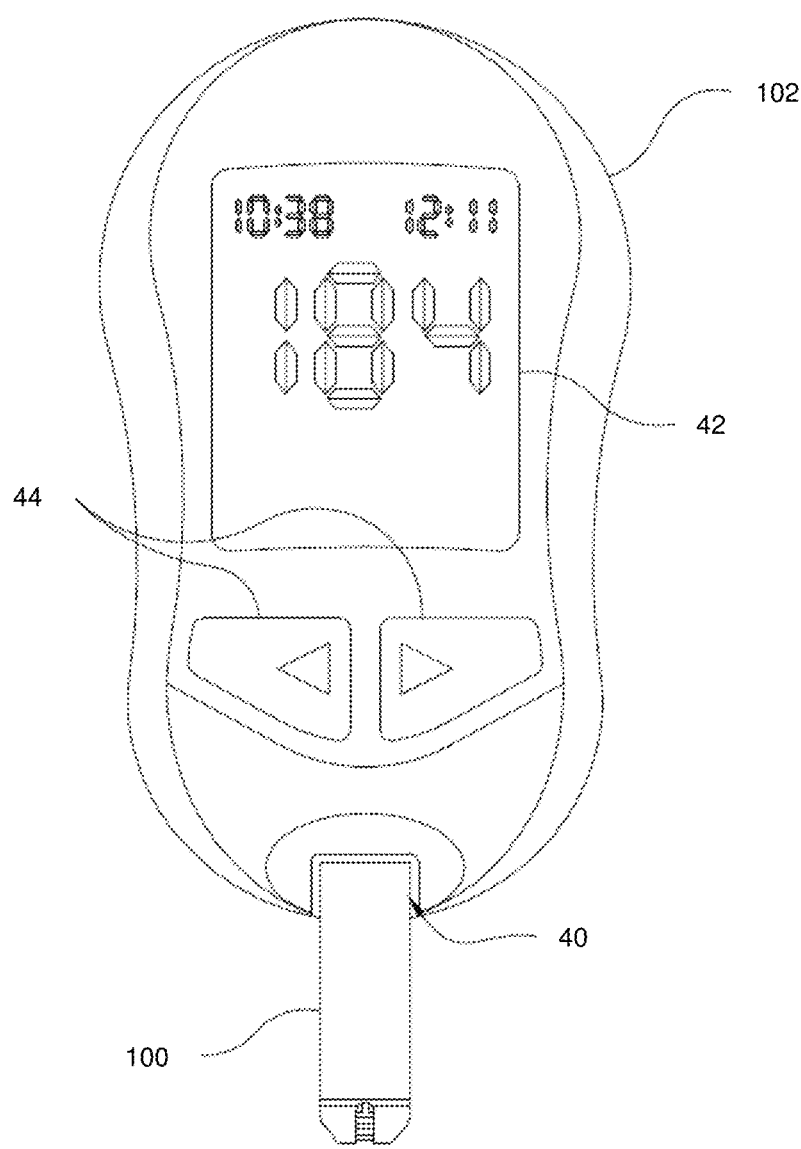
FIG. 5 is a simplified schematic view of an exemplary test system including a measurement device and a biosensor.

In FIG. 5, the biosensor 100 is a single use test element removably inserted into a connection terminal (or biosensor port) 40 of the measurement device 102. As used herein, "biosensor" means a device capable of qualitatively or quantitatively detecting one or more analytes of interest on the basis of, for example, a specific reaction or property of a fluidic sample having or suspected of having the analyte of interest. Biosensors, also called test elements, may be classified into electrical-based sensors, magnetic-based sensors, mass-based sensors, and optical-based sensors according to a detection method associated therewith. Of particular interest herein are electrical-based sensors, especially electrochemical sensors.

In some instances, the biosensor 100 is configured as a dual analyte, such as glucose and ketone, biosensor and includes features and functionalities for electrochemically measuring glucose and ketones. See, e.g., Int'l Patent Application Publication Nos. WO 2014/068024 and WO 2014/068022. In other instances, the biosensor 100 is configured to electrochemically measure other analytes such as, for example, amino acids, antibodies, bacteria, carbohydrates, drugs, lipids, markers, nucleic acids, peptides, proteins, toxins, viruses, and other analytes.

The measurement device 102 generally includes an entry (or input) means 44, a controller, a memory associated with the controller/microcontroller, and a programmable processor associated with the controller and connected with the memory (not shown). In addition, the measurement device 102 includes an output such as an electronic display 42 that is connected to the processor and is used to display various types of information to the user including analyte concentration(s) or other test results. Furthermore, the measurement device 102 includes associated test signal generating and measuring circuits (not shown) that are operable to generate a test signal, to apply the signal to the biosensor 100, and to measure one or more responses of the biosensor 100 to the test signal. The processor also is connected with the connection terminal 40 and is operable to process and record data in memory relating to detecting the presence and/or concentration of the analytes obtained through use of one or more biosensors 100. The connection terminal 40 includes connectors configured to engage with contact pads of the conductive elements. Moreover, the measurement device 102 includes user entry means connected with the processor, which is accessible by a user to provide input to processor, where the processor is further programmable to receive input commands from user entry means and provide an output that responds to the input commands.

The processor also is connected with a communication module or link to facilitate wireless transmissions with the measurement device 102. In one form, the communication link may be used to exchange messages, warnings, or other information between the measurement device 102 and another device or party, such as a caseworker, caregiver, parent, guardian or healthcare provider, including nurses, pharmacists, primary or secondary care physicians and emergency medical professionals, just to provide a few possibilities. The communication link also can be utilized for downloading programming updates for the measurement device 102. By way of non-limiting example, the communication link may be configured for sending and receiving information through mobile phone standard technology, including third-generation (3G) and fourth-generation (4G) technologies, or through BLUETOOTH®, ZIGBEE®, Wibree, ultra-wide band (UWB), wireless local area network (WLAN), General Packet Radio Service (GPRS), Worldwide Interoperability for Microwave Access (WiMAX or WiMAN), Wireless Medical Telemetry (WMTS), Wireless Universal Serial Bus (WUSB), Global System for Mobile communications (GSM), Short Message Service (SMS) or WLAN 802.11x standards.

The controller therefore can include one or more components configured as a single unit or of multi-component form and can be programmable, a state logic machine or other type of dedicated hardware, or a hybrid combination of programmable and dedicated hardware. One or more components of the controller may be of the electronic variety defining digital circuitry, analog circuitry, or both. As an addition or alternative to electronic circuitry, the controller may include one or more mechanical or optical control elements.

In some instances, which include electronic circuitry, the controller includes an integrated processor operatively coupled to one or more solid-state memory devices defining, at least in part, memory. In this manner, the memory contains operating logic to be executed by processor that is a microprocessor and is arranged for reading and writing of data in the memory in accordance with one or more routines of a program executed by the microprocessor.

In addition, the memory can include one or more types of solid-state electronic memory and additionally or alternatively may include the magnetic or optical variety. For example, the memory can include solid-state electronic random access memory (RAM), sequentially accessible memory (SAM) (such as the "First-In, First-Out" (FIFO) variety or the "Last-In First-Out" (LIFO) variety), programmable read only memory (PROM), electrically programmable read only memory (EPROM), or electrically erasable programmable read only memory (EEPROM); or a combination of any of these types. Also, the memory may be volatile, nonvolatile or a hybrid combination of volatile and nonvolatile varieties. Some or all of the memory can be of a portable type, such as a disk, tape, memory stick, cartridge, code chip or the like. Memory can be at least partially integrated with the processor and/or may be in the form of one or more components or units.

In some instances, the measurement device 102 may utilize a removable memory key, which is pluggable into a socket or other receiving means and which communicates with the memory or controller to provide information relating to calibration codes, measurement methods, measurement techniques, and information management. Examples of such removable memory keys are disclosed in U.S. Pat. Nos. 5,366,609 and 5,053,199.

The controller also can include signal conditioners, filters, limiters, analog-to-digital (ND) converters, digital-to-analog (D/A) converters, communication ports, or other types of operators as would occur to one of skill in the art.

Returning to the entry means 44, it may be defined by a plurality of push-button input devices, although the entry means 44 may include one or more other types of input devices like a keyboard, mouse or other pointing device, touch screen, touch pad, roller ball, or a voice recognition input subsystem.

Likewise, the display 42 may include one or more output means like an operator display that can be of a cathode ray tube (CRT) type, liquid crystal display (LCD) type, plasma type, light emitting diode (LED) type, organic light emitting diode (OLED) type, a printer, or the like. Other input and display means can be included such as loudspeakers, voice generators, voice and speech recognition systems, haptic displays, electronic wired or wireless communication subsystems, and the like.

As indicated above, the connection terminal 40 includes connectors configured to engage with contact pads of the conductive elements of the biosensors described herein. The connection between the measurement device 102 and the biosensor 100 is used to apply a test signal having a potential or a series of potentials across the electrodes of the conductive elements and to subsequently receive electrochemical signals that are produced by the detection reagents in the presence of the analytes of interest and can be correlated to the concentration of the analytes. In this manner, the processor is configured to evaluate the electrochemical signals to assess the presence and/or concentration of the analyte, where the results of the same may be stored in the memory.

In some instances, the measurement device 102 can be configured as a blood glucose measurement meter and includes features and functionalities of the ACCU-CHEK® AVIVA® meter as described in the booklet "Accu-Chek® Aviva Blood Glucose Meter Owner's Booklet" (2007), portions of which are disclosed in U.S. Pat. No. 6,645,368. In other instances, measurement device 102 can be configured to electrochemically measure one or more other analytes such as, for example, amino acids, antibodies, bacteria, carbohydrates, drugs, lipids, markers, nucleic acids, proteins, peptides, toxins, viruses, and other analytes. Additional details regarding exemplary measurement devices configured for use with electrochemical measurement methods are disclosed in, for example, U.S. Pat. Nos. 4,720,372; 4,963,814; 4,999,582; 4,999,632; 5,243,516; 5,282,950; 5,366,609; 5,371,687; 5,379,214; 5,405,511; 5,438,271; 5,594,906; 6,134,504; 6,144,922; 6,413,213; 6,425,863; 6,635,167; 6,645,368; 6,787,109; 6,927,749; 6,945,955; 7,208,119; 7,291,107; 7,347,973; 7,569,126; 7,601,299; 7,638,095 and 8,431,408.

In addition to the measurement device 102, the test systems include one more biosensors 10, 100 or 200 as illustrated schematically in FIGS. 2-4 and 6.

Figure 6:
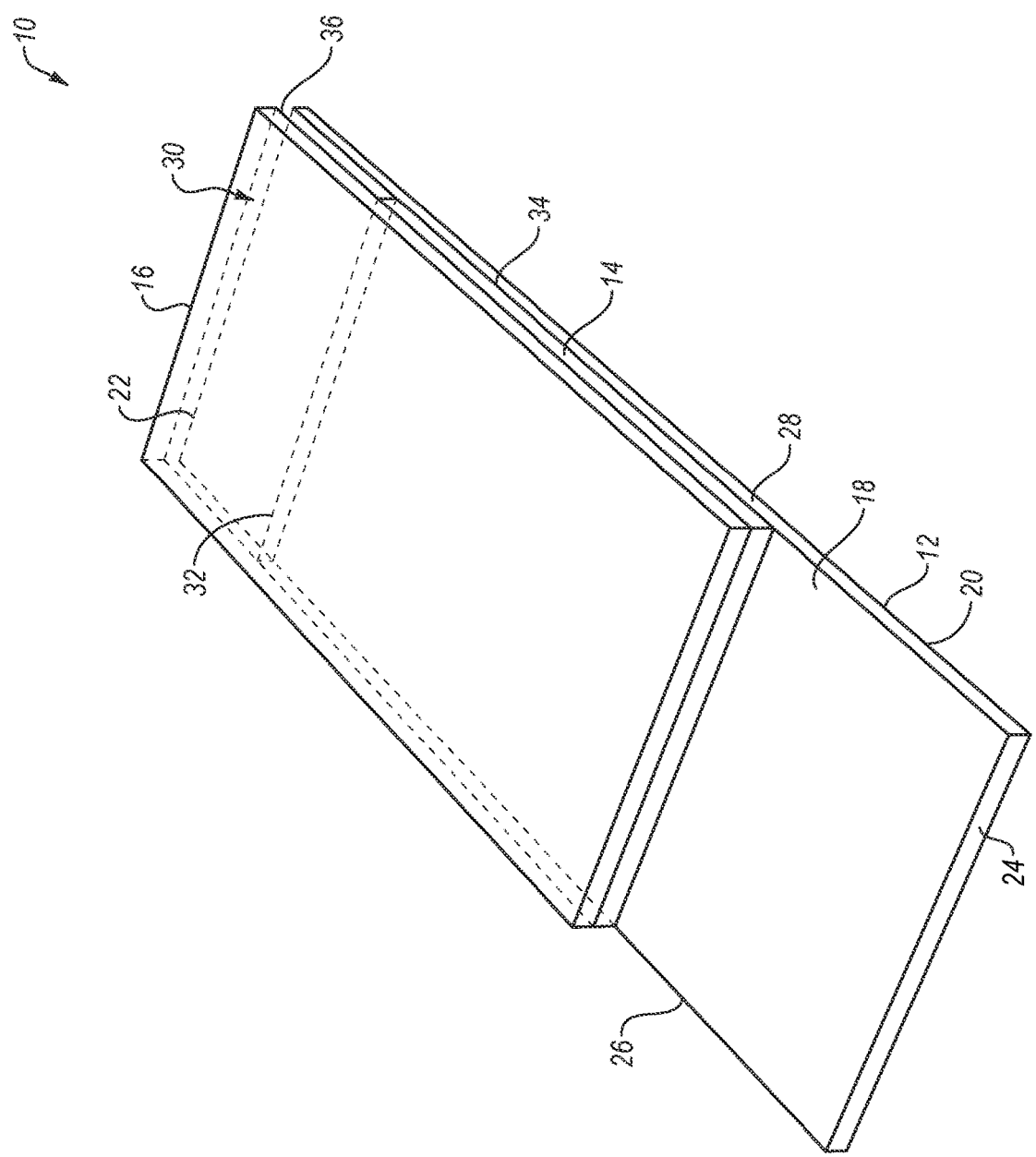
FIG. 6 is a perspective view of an exemplary biosensor or test element in the form of a test strip.

With respect to FIG. 6, a non-conductive support substrate 12 of the biosensor 10 includes a first surface 18 facing the spacer 14 and a second surface 20 opposite the first surface 18. Moreover, the support substrate 12 has opposite first and second ends 22, 24 and opposite side edges 26, 28 that extend between the first and second ends 22, 24. In some instances, the first and second ends 22, 24 and the opposite side edges 26, 28 of the support substrate 12 form a generally rectangular shape. Alternatively, the first and second ends 22, 24 and the opposite side edges 26, 28 may be arranged to form any one of a variety of shapes and sizes that enable the biosensor 10 to function as described herein. In some instances, the support substrate 12 can be fabricated of a flexible polymer including, but not limited to, a polyester or polyimide, such as polyethylene naphthalate (PEN) or polyethylene terephthalate (PET). Alternatively, the support substrate 12 can be fabricated from any other suitable materials that enable the support substrate 12 to function as described herein.

An electrical conductor forming the conductive elements is provided on the first surface 18 of the support substrate 12. The electrical conductor may be fabricated from materials including, but not limited to, aluminum, carbon (e.g., graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., highly doped polycrystalline silicon), silver, tantalum, tin, titanium, tungsten, uranium, vanadium, zinc, zirconium, and combinations thereof. In some instances, the conductive elements are isolated from the rest of the electrical conductor by laser ablation or laser scribing, both of which are well known in the art. In this manner, the conductive elements can be fabricated by removing the electrical conductor from an area extending around the electrodes either broadly, such as by broad field ablation, or minimally, such as by line scribing. Alternatively, the conductive elements may be fabricated by other techniques such as, for example, lamination, screen-printing, photolithography, etc.

In the exemplary embodiment, biosensor 10 has a full width end dose ("FWED") capillary channel 30 that is bounded only on one side and is located at the first end 22 of the support substrate. See, e.g., Int'l Patent Application Publication No. WO 2015/187580. It is contemplated, however, that the capillary channel 30 also can be a conventional capillary channel (i.e., bounded on more than one side).

In a FWED-type biosensor, the spacer 14 extends between the opposite side edges 26, 28 of the support substrate 12 to form the capillary channel 30 in part with a cover. It is contemplated that the spacer 14 may be fabricated of a single component or even a plurality of components. Regardless, the spacer 14 should include an end edge 32 substantially parallel to and facing the first end 22 of the support substrate 12, thereby defining a boundary of a capillary channel 30 by extending across the entire width of the support substrate 12. Alternatively, and as noted above, the end edge 32 may include multiple portions located between the first and second ends 22, 24 and the opposite side edges 26, 28 of the support substrate 12 to form a generally U-shaped pattern to define the boundary of the capillary channel 30 having a sample inlet at the first end 22 of the test element 10 (not shown). Other suitable embodiments contemplate an end edge 28 that forms hemi-ovular, semi-circular, or other shaped capillary channels, and the one or more of the portions of end edge 32 may include linear or non-linear edges along all or part of its length (not shown).

The spacer 14 is fabricated from an insulative material such as, for example, a flexible polymer including an adhesive-coated polyethylene terephthalate (PET)-polyester. One particular non-limiting example of a suitable material includes a PET film, both sides of which can be coated with a pressure-sensitive adhesive. The spacer 14 may be constructed of a variety of materials and includes an inner surface 34 that may be coupled to the first surface 18 of the support substrate 12 using any one or a combination of a wide variety of commercially available adhesives. Additionally, when first surface 18 of the support substrate 12 is exposed and not covered by the electrical conductor, the cover 16 may be coupled to support the substrate 12 by welding, such as heat or ultrasonic welding. It also is contemplated that first surface 18 of the support substrate 12 may be printed with, for example, product labeling or instructions (not shown) for use of the test elements 10.

In some instances, the spacer 14 can be omitted, and the capillary chamber 30 can be defined only by the support substrate 12 and the cover 16. See, e.g., U.S. Pat. No. 8,992,750.

Further, in the exemplary embodiment, the cover 16 extends between the opposite side edges 26, 28 of the support substrate 12 and extends to the first end 22 of the support substrate 12. Alternatively, the cover 16 may extend beyond the first end 22 a predefined distance that enables the biosensor 10 to function as described herein. In the exemplary embodiment, the capillary channel 30 is therefore defined as the space between the cover 16 and the support substrate 12, bounded by the first end 22 and the opposite side edges 26, 28 of the support substrate 12 and the end edge 32 of the spacer 14.

The cover 16 can be fabricated from an insulative material such as, for example, a flexible polymer including an adhesive-coated PET-polyester. One particular non-limiting example of a suitable material includes a transparent or translucent PET film. The cover 16 may be constructed of a variety of materials and includes a lower surface 36 that may be coupled to the spacer 14 using any one or a combination of a wide variety of commercially available adhesives. Additionally, the cover 16 may be coupled to the spacer 14 by welding, such as heat or ultrasonic welding.

Although not shown in FIG. 6, the biosensors include an electrode system having conductive elements such as, but not limited to, at least one CE/WE electrode pair, one or more electrically conductive pathways or traces, and contact pads or terminals of the electrically conductive material provided on, for example, the first surface of the support such that the electrode systems are co-planar. However, it is contemplated that the electrode system can be formed on opposing surfaces such that one electrode system is on the first surface of the support and another electrode system is on an opposing surface of the cover. See, e.g., U.S. Pat. No. 8,920,628. Regardless, the electrically conductive material typically is arranged on the substrate in such a way to provide the one or more conductive elements.

Particular arrangements of electrically conductive material may be provided using a number of techniques including chemical vapor deposition, laser ablation, lamination, screen-printing, photolithography, and combinations of these and other techniques. One particular method for removing portions of the electrically conductive material include laser ablation or laser scribing, and more particularly broad field laser ablation, as disclosed in, for example, U.S. Pat. Nos. 7,073,246 and 7,601,299. In this manner, the conductive elements can be fabricated by removing electrically conductive material from the substrate either broadly, such as by broad field ablation, or minimally, such as by line scribing. Alternatively, the conductive elements may be fabricated by other techniques such as, for example, lamination, screen-printing, photolithography, etc.

Briefly, laser ablative techniques typically include ablating a conductive material such as a metallic layer or a multi-layer composition that includes an insulating material and a conductive material (e.g., a metallic-laminate of a metal layer coated on or laminated to an insulating material). The metallic layer may contain pure metals, alloys, or other materials, which are metallic conductors. Examples of metals or metallic-like conductors include, but are not limited to, aluminum, carbon (such as graphite and/or graphene), copper, gold, indium, nickel, palladium, platinum, silver, titanium, mixtures thereof, and alloys or solid solutions of these materials. In one aspect, the materials are selected to be essentially unreactive to biological systems, with non-limiting examples including, but not limited to, gold, platinum, palladium, carbon and iridium tin oxide. The metallic layer may be any desired thickness that, in one particular form, is about 500 Å.

As used herein, "about" means within a statistically meaningful range of a value or values including, but not limited to, a stated concentration, length, width, height, angle, weight, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

With respect to the biosensors herein, exemplary conductive elements can include one or more of a WE, WE trace, and WE contact pad, where the conductive trace portions extend between and electrically couple a WE to its respective contact pad. Likewise, the electrically conductive pathways include one or more of a CE, CE trace, and CE contact pad, where the conductive trace portions extend between and electrically couple a CE and to its respective contact pad. As used herein, a "working electrode" or "WE" means an electrode at which an analyte is electrooxidized or electroreduced with or without the agency of a mediator, while the term "counter electrode" or "CE" means an electrode that is paired with one or more WEs and through which passes an electrochemical current equal in magnitude and opposite in sign to the current passed through the WE. CE also includes counter electrodes that also function as reference electrodes (i.e., counter/reference electrodes).

As noted above, the conductive elements include one or more voltage-sensing leads (i.e., Kelvin connections), where such leads can be in the form of a WE voltage-sensing (WES) trace in electrical communication (i.e., via a wire) at one end with the WE or WE trace and terminating at its other end at a WES contact pad, as well as a CE voltage-sensing (CES) trace in electrical communication at one end with the CE or CE trace and terminating at its other end at a CES contact pad. See, e.g., Int'l Patent Application Publication No. 2013/017218. Additional details regarding voltage-sensing traces and their compensation functionality can be found in, for example, U.S. Pat. No. 7,569,126.

The conductive elements also can include one or more sample sufficiency electrodes (SSE), SSE contact pads, and respective SSE traces that extend between and electrically couple the SSEs and SSE contact pads. If included, the SSEs can be used to implement a number of techniques for determining the sufficiency of a sample applied to the biosensors. See, e.g., Int'l Patent Application Publication No. WO 2014/140170 and WO 2015/187580.

The conductive elements also can include one or more integrity electrodes (IE) that can be used to verify that the conductive elements are intact, as described in Int'l Patent Application Publication No. WO 2015/187580.

The conductive elements also can include an information circuit in the form of a plurality of selectable resistive elements that form a resistance network, as described in Int'l Patent Application Publication No. WO 2013/017218 and US Patent Application Publication No. 2015/0362455. The information encoded in the resistance network can relate to an attribute of the biosensors including, but not limited to, calibration information, biosensor type, manufacturing information and the like.

Additional details regarding exemplary diagnostic test element configurations that may be used herein are disclosed in, for example, Int'l Patent Application Publication Nos. WO 2014/037372, 2014/068022 and 2014/068024; US Patent Application Publication Nos. 2003/0031592 and 2006/0003397; and U.S. Pat. Nos. 5,694,932; 5,271,895; 5,762,770; 5,948,695; 5,975,153; 5,997,817; 6,001,239; 6,025,203; 6,162,639; 6,207,000; 6,245,215; 6,271,045; 6,319,719; 6,406,672; 6,413,395; 6,428,664; 6,447,657; 6,451,264; 6,455,324; 6,488,828; 6,506,575; 6,540,890; 6,562,210; 6,582,573; 6,592,815; 6,627,057; 6,638,772; 6,755,949; 6,767,440; 6,780,296; 6,780,651; 6,814,843; 6,814,844; 6,858,433; 6,866,758; 7,008,799; 7,025,836; 7,063,774; 7,067,320; 7,238,534; 7,473,398; 7,476,827; 7,479,211; 7,510,643; 7,727,467; 7,780,827; 7,820,451; 7,867,369; 7,892,849; 8,180,423; 8,298,401; 8,329,026; RE42560; RE42924 and RE42953.

Methods

Methods herein can include compensating, correcting and/or minimizing for $R_{UNC}$ in the conductive paths of conductive elements of biosensors during electrochemical analyte measurements. The methods can include the steps described herein, and these steps may be, but not necessarily, carried out in the sequence as described. Other sequences, however, also are conceivable. Moreover, individual or multiple steps may be carried out either in parallel and/or overlapping in time and/or individually or in multiply repeated steps. Furthermore, the methods may include additional, unspecified steps.

As noted above, an inventive concept herein includes improving accuracy and reliability of analyte measurement systems by correcting, compensating, and/or minimizing for $R_{UNC}$ along the conductive paths of the conductive elements of biosensors used in connection with electrochemical measurements by theoretically segmenting areas of the conductive elements (e.g., CE and WE) into a number of conductive squares. The methods therefore can include determining one or more $R_s$ and then $R_{UNC}$ present in the conductive elements of biosensors, which accounts for the number of conductive squares, and subsequently subtracting $R_{UNC}$ from a real portion of a relevant impedance measurement. Alternatively, the $R_{UNC}$ may be used to correct a measured impedance calculation to minimize inaccuracies due to the value or variations in the conductive elements' $R_s$.

Accordingly, FIG. 7 shows a simplified diagram of a coplanar, two electrode biosensor 600 having conductive elements such as two voltage-sensing (or reference) traces (indicated by cross-hatch; WE sense trace 602, CE sense trace 604), a WE trace 606, a CE trace 608, a WE 610, a CE 612, and a reaction zone 614 (indicated by light shading). Within the reaction zone 614, the entire or majority of a loop current ($I_{LOOP}$, $I_A$-$I_H$; shown in FIG. 9) can be distributed along active portions 620, 622 of the WE 610 and CE 312, respectively. In contrast, an end 624 of the WE 610, and an end 626 of the CE 612, which are not in contact with a sample within the reaction zone 614, may not contribute to any reaction-dependent current generated between the active portions 620, 622. As such, the WE 610 includes uncompensated connecting portion 616, active portion 620, and end 624. Likewise, the CE 612 includes uncompensated connecting portion 618, active portion 622, and end 626.

The voltage-sensing traces 602, 604 can be coupled to a measurement device, as described above, and can connect to a high input impedance, thereby reducing the current in the voltage-sensing traces 602, 604 to near 0 nA. By reducing or eliminating current flow in the voltage-sensing traces 602, 604, the voltage differential applied at the CE 612 and WE 610 is not affected by the impedance of the voltage-sensing traces 602, 604.

In FIG. 7, locations 'X' and 'Y' indicate an area where uncompensated connecting portions 616, 618 of the WE 610 and the CE 612 begin (i.e., 'after' sense connections, where the sense connections are indicated as points X and Y). Between points X and Y, the true voltage potential difference across a load can be variable and less than the voltage provided by the measuring device (not shown) due to ohmic losses along uncompensated connecting portions 616, 618.

Figure 8:
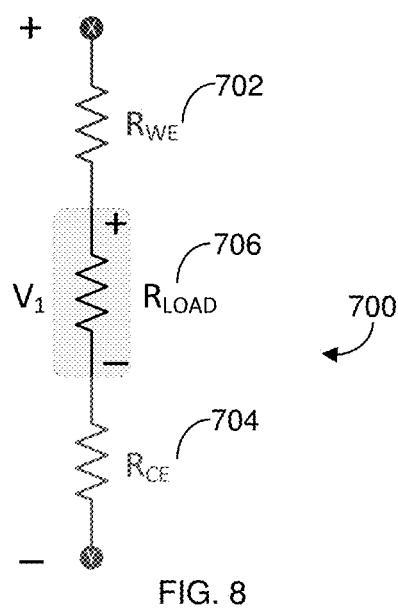
FIG. 8 is a simplified schematic example of the measuring circuit of the two electrode biosensor of FIG. 7.

As shown in FIG. 8, the true load impedance between the uncompensated active portions 620, 622 is, therefore, in series with the uncompensated connecting portions 616, 618 of the WE 610 and the CE 612, respectively, and can be represented as a pair of lumped resistors $R_{WE}$ and $R_{CE}$. More specifically, a measuring circuit 700 can be modelled as collection of resistive elements that includes a first resistor ($R_{WE}$) 702 representing the lumped resistance of the uncompensated connecting portion 616 of the WE 610 and a second resistor ($R_{CE}$) 704 representing the lumped resistance of the uncompensated connecting portion 618 of the CE 612. A load resistor ($R_{LOAD}$) 706 represents the true impedance between the uncompensated active portions 620, 622 of the WE 610 and the CE 612. A properly designed measuring circuit therefore will attempt to limit currents in the voltage-sensing traces to zero and to maintain a potential difference of $V_1$ between points X and Y.

As shown in FIG. 9, the above-described model can be extended to the system 600 of FIG. 7. In particular, FIG. 9 shows a simple approximation of the total number of uncompensated conductive squares in the active portions of WE 610 and CE 612, where the undesirable influence of additional resistance is an uncompensated I×R loss between points X and Y. As either I or R increases, the mean potential difference between the electrodes decreases. Moreover, conductive squares carrying larger currents will have a proportionally larger impact than conductive squares carrying lesser currents.

Here, the uncompensated connecting portion 616, the uncompensated active portion 620, and end 624 of the WE 610, as well as the uncompensated connecting portion 618, the uncompensated active portion 622, and the end 626 of the CE 612, are theoretically segmented into a number of conductive squares 802, 804. For example, these portions can be divided into twelve (12) conductive squares 802a-802l, 804a-804l, respectively. One of skill in the art, however, understands that the number of conductive squares to which these portions of the CE and WE are divided can and will vary depending upon the architecture of a biosensor's conductive elements.

In one configuration, the uncompensated connecting portion 616 of the WE 610 can be represented by WE conductive squares 802a-802c, and the uncompensated connecting portion 618 of the CE 612 can be represented by CE conductive squares 804a-804c. Moreover, the uncompensated active portion 620 of the WE 610 can be represented by WE conductive squares 802d-802k, and the uncompensated active portion 622 the CE 612 can be represented and CE conductive squares 804d-804k. Furthermore, the end 624 of the WE 610 can be represented by WE conductive square 802l, and the end 626 of the CE 612 can be represented by CE conductive square 804l. As noted above, the ends 624, 626 are not in contact with a sample and therefore do not contribute to any reaction-dependent current that would be generated between the uncompensated active portions 620, 622.

The entire $I_{LOOP}$ can flow through CE trace 608 and CE conductive squares 804a-804k. In this regard, the $I_{LOOP}$ can be uniformly distributed along eight (8) CE conductive squares 804d-804k, shown as $I_A$-$I_H$. In some instances, the current may not be not symmetrically distributed across CE conductive squares 804d-804k. For example, current $I_H$ flowing between CE conductive square 804d and WE conductive square 802k can be substantially greater than the current $I_A$ flowing between CE conductive square 804k and WE conductive square 802d. In general, however, the current distribution along the WE 610 mirrors the current distribution of the CE 612.

Figure 10:
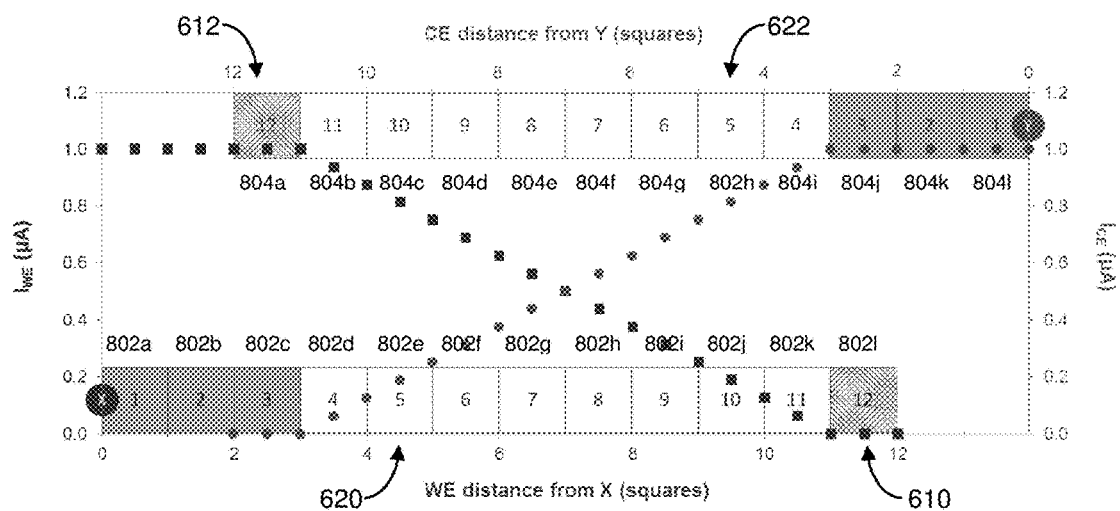
FIG. 10 is a current distribution plot illustrating current values flowing between the electrodes in the two-electrode biosensor of FIG. 7. The WE current ($I_{WE}$) in µA is represented by squares, and the CE current ($I_{CE}$) in µA is represented by circles.

As shown in FIG. 10, current can be plotted along the WE 610 and CE 612 as a function of distance. Here, the current along the WE 610 starts from 0 at WE conductive square 802l (outside the reaction zone), increases along WE conductive squares 802k-802d, and reaches the full $I_{LOOP}$ by WE conductive square 802c. Thus, the total current, $I_{LOOP}$, can be expressed by the following equation:

$$I_{LOOP} = \Sigma_A^H I_N \text{ and } I_A \approx I_B \approx I_C \approx I_D \approx I_E \approx I_F \approx I_G \approx I_H \qquad \text{Equation 2}$$

Stated differently, the active current can be evenly divided between the eight (8) conductive squares in each uncompensated active portion 620, 622 (true current will be a linear function of the actual potential difference between the electrodes). The total WE current accumulates moving from right to left (i.e., WE conductive squares 802I to 802c) in FIG. 9. The current in WE conductive square 802I is zero since it is outside the active portion 620. The current entering the right edge of WE conductive square 802k is 0, and the current leaving the left edge of square 802k is $I_H$. Similarly, the current leaving the left edge of WE conductive square 802j is $[I_G+I_H]$. This continues through WE conductive square 802d. Each uncompensated conductive square in active portion 620 carries a portion of the $I_{LOOP}$ current, increasing as the distance to point X decreases. Approximately ⅞ of $I_{LOOP}$ enters the right edge of WE conductive square 802d, and the entire $I_{LOOP}$ passes through the left edge of WE conductive square 802d. The WE of FIG. 9 has three uncompensated connecting squares (802a-c) that carry the entire WE $I_{LOOP}$ current. Since I×R loss is a primary influence to measurement error, conductive squares carrying only a fraction of $I_{LOOP}$ do not contribute as substantially to potential error as squares carrying the entire loop current. Therefore, one can estimate each WE conductive square's current as the right-left mean as follows:

$$802k \; I \times R \; \text{drop} \approx \left[\frac{I_H + 0}{2}\right] \times (R_s \times 1 \; sq) = \frac{\frac{I_{LOOP}}{8}}{2} \times (R_s \times 1 \; sq); \qquad \text{Equation 3}$$

$$802j \; I \times R \; \text{drop} \approx \left[\frac{(I_G + I_H) + I_H}{2}\right] \times (R_s \times 1 \; sq) = \frac{\frac{3 \times I_{LOOP}}{8}}{2} \times (R_s \times 1 \; sq); \qquad \text{Equation 4}$$

$$802i \; I \times R \; \text{drop} \approx \left[\frac{(I_F + I_G + I_H) + (I_G + I_H)}{2}\right] \times (R_s \times 1 \; sq) = \frac{\frac{5 \times I_{LOOP}}{8}}{2} \times (R_s \times 1 \; sq); \qquad \text{Equation 5}$$

$$802h \; I \times R \; \text{drop} \approx \left[\frac{(I_E + I_F + I_G + I_H) + (I_F + I_G + I_H)}{2}\right] \times (R_s \times 1 \; sq) = \frac{\frac{7 \times I_{LOOP}}{8}}{2} \times (R_s \times 1 \; sq); \qquad \text{Equation 6}$$

$$802g \; I \times R \; \text{drop} \approx \left[\frac{(I_D + I_E + I_F + I_G + I_H) + (I_E + I_F + I_G + I_H)}{2}\right] \times (R_s \times 1 \; sq) = \frac{\frac{9 \times I_{LOOP}}{8}}{2} \times (R_s \times 1 \; sq); \qquad \text{Equation 7}$$

$$802f \; I \times R \; \text{drop} \approx \left[\frac{(I_C + I_D + I_E + I_F + I_G + I_H) + (I_D + I_E + I_F + I_G + I_H)}{2}\right] \times (R_s \times 1 \; sq) = \frac{\frac{11 \times I_{LOOP}}{8}}{2} \times (R_s \times 1 \; sq); \qquad \text{Equation 8}$$

$$802e \; I \times R \; \text{drop} \approx \left[\frac{(I_B + I_C + I_D + I_E + I_F + I_G + I_H) + (I_C + I_D + I_E + I_F + I_G + I_H)}{2}\right] \times (R_s \times 1 \; sq) = \frac{\frac{13 \times I_{LOOP}}{8}}{2} \times (R_s \times 1 \; sq); \qquad \text{Equation 9}$$

-continued

802d $I \times R$ drop $\approx$    Equation 10

$$\left[\frac{(I_A + I_B + I_C + I_D + I_E + I_F + I_G + I_H) +}{2}\right] \times (R_s \times 1 \ sq) =$$

$$\frac{15 \times I_{LOOP}}{2} \times (R_s \times 1 \ sq);$$

802c $I \times R$ drop $\approx$    Equation 11

$$\left[\frac{I_{LOOP} + I_{LOOP}}{2}\right] \times (R_s \times 1 \ sq) = I_{LOOP} \times (R_s \times 1 \ sq);$$

802b $I \times R$ drop $\approx$    Equation 12

$$\left[\frac{I_{LOOP} + I_{LOOP}}{2}\right] \times (R_s \times 1 \ sq) = I_{LOOP} \times (R_s \times 1 \ sq);$$

802a $I \times R$ drop $\approx$    Equation 13

$$\left[\frac{I_{LOOP} + I_{LOOP}}{2}\right] \times (R_s \times 1 \ sq) = I_{LOOP} \times (R_s \times 1 \ sq); \text{ and}$$

total $I \times R$ Drop $\approx$    Equation 14

$$\left[\left[3 + \frac{15}{16} + \frac{13}{16} + \frac{11}{16} + \frac{9}{16} + \frac{7}{16} + \frac{5}{16} + \frac{3}{16} + \frac{1}{16}\right] \times I_{LOOP}\right] \times (Rs \times 1 \ sq) = 7 I_{LOOP} \times (Rs \times 1 \ sq).$$

As noted above, not every conductive square carries the same current. Each active square carries only a portion of the total current, so the average active current can be estimated as $I_{LOOP}/2$. In this manner, a simple approximation of the total $R_{WE}$ and likewise the total $R_{CE}$ can be calculated as the individual trace resistivity multiplied by the conductive squares outside the reaction zone (i.e., the conductive squares in the uncompensated connecting portions 616, 618 of the CE or WE) plus half of the conductive squares in the reaction zone (i.e., the conductive squares in the uncompensated active portions 620, 622 of the CE or WE). Thus, for the system 600 shown in FIGS. 7 and 9, a simple approximation of $R_{UNC}$ for the WE and CE (i.e., $R_{WE}$ and $R_{CE}$) can be by multiplying $R_s$ by the three (3) conductive squares outside the reaction zone plus half of the eight (8) conductive squares in the reaction zone (i.e., $I_{LOOP}/2$), which can be calculated as follows:

$$R_{WE} = R_{CE} \sim \left(\frac{1.0\Omega}{\text{square}}\right) \times \left(3 \text{ squares} + \frac{8 \text{ squares}}{2}\right) = 7\Omega$$

Figures 11, 12:
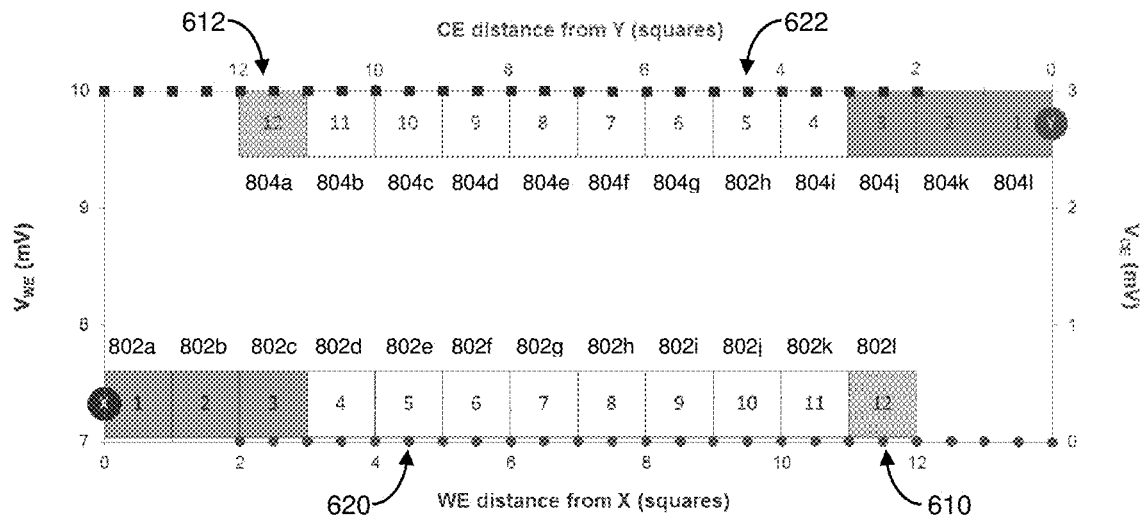
FIG. 11 is a voltage potential distribution plot illustrating voltage potentials between the electrodes in the two-electrode biosensor of FIG. 7. The WE voltage ($V_{WE}$) in mV is represented by squares, and the CE voltage ($V_{CE}$) in µA is represented by circles.
FIG. 12 is a current distribution plot illustrating current values between the electrodes in the two-electrode biosensor of FIG. 7 with a 300Ω load. The WE current ($I_{WE}$) in µA is represented by squares, and the CE current ($I_{CE}$) in µA is represented by circles.

Thus, if the above system 600 is connected to an ideal 10 kC) load and $|V_1|=10$ mV, the measured $I_{LOOP}$ of a biosensor would equal 10 mV/(14Ω+10 kΩ))=0.9986 ρA, and the computed "load" resistance equals 10.014 kC) (+0.14% error). The corresponding WE-CE potential difference would be an effectively constant 10 mV, as shown in FIG. 11. Alternatively, if the above system 600 is connected to an ideal load of 300Ω, and $|V_1|=10.0$ mV, the measured $I_{LOOP}$ of a biosensor would equal 10 mV/(14Ω+300Ω))=31.85 ρA, and the computed "load" resistance would equal 314Ω (+4.46% error). Further, the corresponding WE-CE potential difference would be ≤10 mV, as shown in FIG. 12. One of skill in the art, however, understands that real world trace current can be more complex, and may not flow along ideal orthogonal paths.

Figure 13:
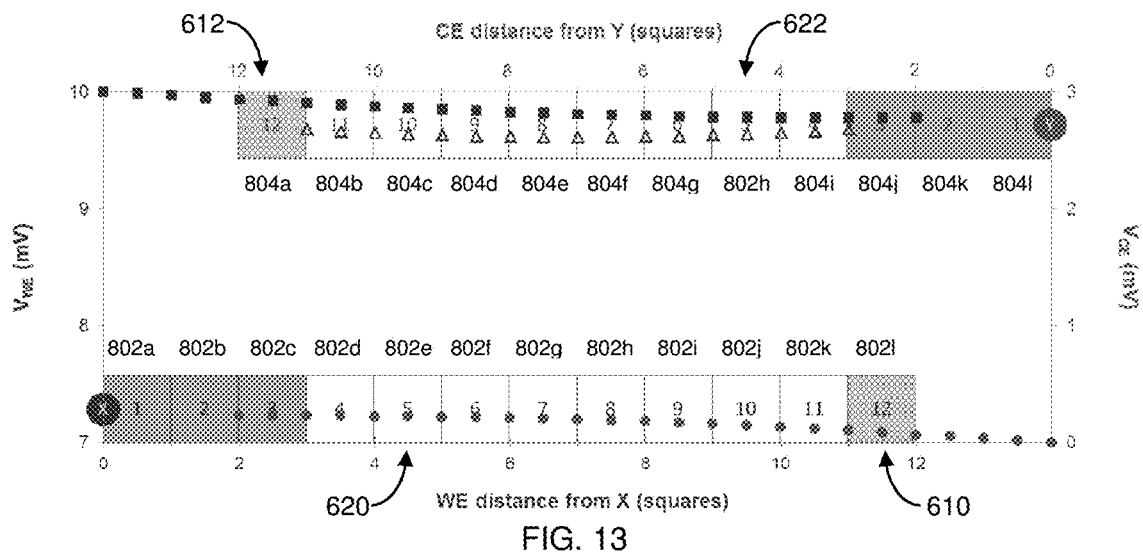
FIG. 13 is a voltage distribution plot illustrating possible voltage potential difference errors in a two-electrode biosensor having a uniform current distribution in the measurement cell for a $R_s$ of 1 Ω/square. The WE voltage ($V_{WE}$) in mV is represented by squares (■), and the CE voltage ($V_{CE}$) in µA is represented by circles (●). The potential difference error is represented by triangles (▲).
Figure 14:
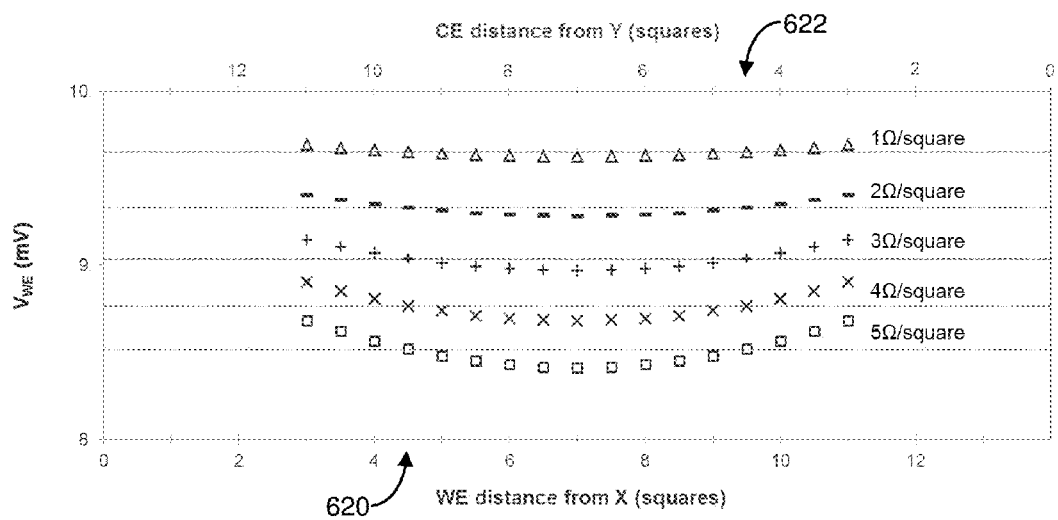
FIG. 14 demonstrates possible potential difference errors for other sheet resistances when measuring a distributed 300Ω load using the two-electrode biosensor of FIG. 7. Potential difference errors at 1 Ω/square, 2 Ω/square, 3 Ω/square, 4 Ω/square and 5 Ω/square are represented by triangles, dashes, pluses, X's and squares, respectively.

FIG. 13 shows the potential difference error using a uniform current distribution in the measurement cell for a $R_s$ of 1 Ω/square. More specifically, FIG. 14 shows possible potential difference errors for other sheet resistances when measuring a distributed 300Ω load using the exemplary electrode arrangement of FIGS. 7 and 9. As can be seen, as $R_s$ increases so too does the potential drop (not constant over WE and CE conductive squares 802d-802k and 804d-804k, respectively, within WE and CE uncompensated active portions 620, 622).

Thus, and as shown above, electrode cell design and trace connection can reduce an amount of $R_{UNC}$ not accounted for by voltage-sensing traces and can control the active potential error to a desirable value. However, a given biosensor design can be restricted by system requirements, physical size, cost constraints, or design complexity. Moreover, $R_s$ of printed or sputtered conductive films can be difficult to precisely control and may vary from lot to lot.

A typical conductor's $R_s$ is a function of electron concentration and mobility. Above 100 K, a metallic conductor's sheet resistance will generally increase linearly with temperature. The opposite is true for carbon or semiconductor materials. For carbon or semiconductor materials, the $R_s$ generally decreases (non-linearly) with increasing temperature up to about 250 K. Similar principles can apply to a liquid sample. For example, an increase in solution temperature can decrease its viscosity and increase the mobility of the ions in solution, thereby decreasing its bulk resistance. Precision conductors created from printing or sputtering therefore are generally not cost effective. Additionally, tolerable production variations may impose unacceptable errors in precision impedance measurements. Thus, for improved accuracy and wider measurement ranges, the mechanisms provided herein can be used to correct (at the time of use) measurements of otherwise unknown impedances on biosensors made from low conductivity or highly variable $R_s$ conductors.

The correcting/compensating/minimizing methods described herein thus can be incorporated into known analyte measuring methods to correct uncompensated resistances in the conductive elements of electrochemical biosensors, thereby improving analyte measurement systems that use such biosensors.

In view of the above, the methods can begin by applying a body fluid having or suspected of having one or more analytes of interest therein to a biosensor. After the body fluid sample has been applied to a dosing end of the biosensor and rehydrates the detection reagents, the analyte measurement methods include applying a test sequence of one or more potentials to the conductive elements of the biosensor. Such a test sequence can be applied by the measurement device from its connection terminals to one or more contact pads of the conductive elements.

In general, test sequences include one or more AC components (optional) and/or one or more DC components as are known in the art. See, e.g., Int'l Patent Application Publication Nos. WO 2014/140718; WO 2014/140164; WO 2014/140170; WO 2014/140172; WO 2014/140173; and WO 2014/140177, as well as U.S. Pat. Nos. 7,338,639; 7,390,667; 7,407,811; 7,417,811; 7,452,457; 7,488,601; 7,494,816; 7,597,793; 7,638,033; 7,751,864; 7,977,112; 7,981,363; 8,148,164; 8,298,828; 8,377,707 and 8,420,404.

For impedance measurements, the test sequence therefore should include at least one AC component. Such a component can include a plurality of AC segments such as, for example, from about 2 segments to about 10 segments, from about 3 segments to about 9 segments, from about 4 segments to about 8 segments, from about 5 segments to about 7 segments, or about 6 segments. In other instances, the AC component can include about 2 segments, about 3 segments, about 4 segments, about 5 segments, about 6 segments, about 7 segments, about 8 segments, about 9 segments, or about 10 segments. In still other instances, the AC component can have more than 10 segments, that is, about 15 segments, about 20 segments, or about 25 segments. In yet other instances, the AC component can include 1 segment, where the segment has multiple low-frequency AC signals applied simultaneously.

One of skill in the art understands that the number of AC segments will be limited by the complexity of the response, the associated frequency range and time available to perform the measurements. Higher frequencies generally require high bandwidth electronics and faster sampling, whereas lower frequencies take longer and typically are noisier. The maximum number of segments therefore will be a compromise of these parameters, choosing the minimum count and frequency span needed to discriminate the sample and environmental and/or confounding factors of interest.

The frequency of each signal in each segment of the AC component can be from about 1 kHz to about 20 kHz, from about 2 kHz to about 19 kHz, from about 3 kHz to about 18 kHz, from about 4 kHz to about 17 kHz, from about 5 kHz to about 16 kHz, from about 6 kHz to about 15 kHz, from about 7 kHz to about 14 kHz, from about 8 kHz to about 13 kHz, from about 9 kHz to about 12 kHz or from about 10 kHz to about 11 kHz. In other instances, the frequency of each segment in the AC component can be about 1 kHz, about 2 kHz, about 3 kHz, about 4 kHz, about 5 kHz, about 6 kHz, about 7 kHz, about 8 kHz, about 9 kHz, about 10 kHz, about 11 kHz, about 12 kHz, about 13 kHz, about 14 kHz, about 15 kHz, about 16 kHz, about 17 kHz, about 18 kHz, about 19 kHz, or about 20 kHz. In still other instances, the frequency of each signal in each segment of the AC component can be more than 20 kHz, that is, about 30 kHz, about 40 kHz, or about 50 kHz. In some instances, one or more of the segments can have the same frequency, whereas in other instances each segment has a distinct frequency from the other segments. Four frequencies, however, generally is adequate. The exact frequencies employed can be readily generated by simple integer division of a measurement system clock's maximum frequency.

A maximum frequency limit for a signal in a segment of the AC component, however, can be up to about 100 kHz for an inexpensive, battery-powered handheld instrument such as the meter. Beyond that, the increasing demands on analog bandwidth, sampling rate, storage and processing speed quickly add up, while the imaginary portion of a typical biosensor response becomes increasingly smaller with frequency. Lower frequencies have longer periods and take longer times to sample with comparable accuracy.

The AC component typically includes at least two (2) different low-amplitude signals. For example, the AC component can include two (2) segments at two (2) frequencies such as, for example, about 10 kHz or about 20 kHz followed by about 1 kHz or about 2 kHz. In other instances, the AC component includes a plurality of low-amplitude signals. For example, the AC component can have five (5) segments at four (4) frequencies such as, for example, about 10 kHz, about 20 kHz, about 10 kHz, about 2 kHz and about 1 kHz. Alternatively, the AC component can have four (4) segments at four (4) frequencies such as, for example, about 20 kHz, about 10 kHz, about 2 kHz and about 1 kHz. Alternatively, the AC component can have four (4) frequencies applied simultaneously at about 10 kHz, about 20 kHz, about 10 kHz, about 2 kHz and about 1 kHz. Alternately still, the AC component can have a multi-frequency excitation waveform that simultaneously applies the desired low-amplitude AC signals. The AC frequencies may be applied sequentially, or combined and applied simultaneously and analyzed via Fourier Transform.

The component of low-amplitude AC signals can be applied for about 500 msec to about 1.5 sec, about 600 msec to about 1.25 sec, about 700 msec to about 1000 msec, or about 800 msec to about 900 msec. Alternatively, the component of low-amplitude AC signals can be applied for about 500 msec, about 600 msec, about 700 msec, about 800 msec, about 900 msec, about 1000 msec, about 1.25 sec or about 1.5 sec. In particular, the component of low-amplitude AC signals can be applied for about 100 msec to about 300 msec.

One of skill in the art, however, understands that the number, frequency, duration and order of the AC segments can be varied.

AC current response information can be obtained at any time during a test sequence. Impedance results at lower frequencies may be influenced by analyte concentration if obtained after an electrochemical cell is DC polarized. In some instances, a series of AC current response measurements can be obtained early in the test sequence. Measurements taken shortly after a fluidic sample is applied to a test element will be influenced by diffusion, temperature and reagent solubility. In other instances, the AC response current measurements can be obtained at a sufficient time after an adequate sample has been applied to allow the response to stabilize, and avoid the transient response in the first second. Likewise, response current measurements can be made at one or more frequencies. Due to their capacitive nature, multiple AC measurements separated by a frequency octave or decade may offer different sensitivities or easier manipulation.

Additional details regarding exemplary AC components in electrochemical measurement methods are disclosed in, for example, U.S. Pat. Nos. 7,338,639; 7,390,667; 7,407,811; 7,417,811; 7,452,457; 7,488,601; 7,494,816; 7,597,793; 7,638,033; 7,751,864; 7,977,112; 7,981,363; 8,148,164; 8,298,828; 8,377,707 and 8,420,404.

The test sequence also can include one or more DC components. Such a component can include a plurality of pulses such as, for example, from about 2 pulses to about 10 pulses, from about 3 pulses to about 9 pulses, from about 4 pulses to about 8 pulses, from about 5 pulses to about 7 pulses, or about 6 pulses. In other instances, the DC component can include about 2 pulses, about 3 pulses, about 4 pulses, about 5 pulses, about 6 pulses, about 7 pulses, about 8 pulses, about 9 pulses, or about 10 pulses. In still other instances, the DC component can have more than 10 pulses, that is, about 15 pulses, about 20 pulses, or about 25 pulses. As used herein, "pulse" means at least one excitation and one recovery period.

The DC component typically includes a constantly applied potential difference that alternates between about 0 mV and about +450 mV potential difference, or other slowly time-varying potential difference that can be analyzed by traditional DC electrochemical methods. One of skill in the art, however, understands that the range for the applied potential difference can, and will, vary depending upon the analyte and reagent chemistry used. As such, excitation pulse potential can be greater-than, less-than or equal to about +450 mV. Examples of excitation potentials include, but are not limited to, 50 mV, 75 mV, 100 mV, 125 mV, 150 mV, 175 mV, 200 mV, 225 mV, 250 mV, 275 mV, 300 mV, 325 mV, 350 mV, 375 mV, 400 mV, 425 mV, 450 mV, 475 mV, 500 mV, 525 mV, 550 mV, 575 mV, 600 mV, 625 mV, 650 mV, 675 mV, 700 mV, 725 mV. 750 mV, 775 mV, 800 mV, 825 mV, 850 mV, 875 mV, 900 mV, 925 mV, 950 mV, 975 mV or 1000 mV.

Regardless of the number, each DC pulse can be applied for about 50 msec to about 500 msec, about 60 msec to about 450 msec, about 70 msec to about 400 msec, about 80 msec to about 350 msec, about 90 msec to about 300 msec, about 100 msec to about 250 msec, about 150 msec to about 200 msec, or about 175 msec. Alternatively, each pulse can be applied for about 50 msec, about 60 msec, about 70 msec, about 80 msec, about 90 msec, about 100 msec, about 125 msec, about 150 msec, about 175 msec, about 200 msec, about 225 msec, about 250 msec, about 275 msec, about 300 msec, about 325 msec, about 350 msec, about 375 msec, about 400 msec, about 425 msec, about 450 msec, about 475 msec or about 500 msec. In particular, each DC pulse at +450 mV can be applied for about 250 msec, and each DC pulse at 0 mV can be applied for about 500 msec. Alternatively still, each pulse can be applied for less than about 50 msec or more than about 500 msec.

Generally, the ramp rate of each DC pulse is selected to provide about 50% or greater reduction in peak current relative to the peak current provided by a nearly ideal potential transition. In some instances, each pulse can have the same ramp rate. In other instances, some pulses can have the same ramp rate and other pulses can have a different ramp rate. In still other instances, each pulse has its own ramp rate. For example, effective ramp rates can be from about 5 mV/msec to about 75 mV/msec or from about 10 mV/msec to about 50 mV/msec, 15 mV/msec to about 25 mV/msec, or about 20 mV/msec. Alternatively, the ramp rate can be about 5 mV/msec, about 10 mV/msec, about 15 mV/msec, about 20 mV/msec, about 25 mV/msec, about 30 mV/msec, about 35 mV/msec, about 40 mV/msec, about 45 mV/msec, about 50 mV/msec, about 55 mV/msec, about 60 mV/msec, about 65 mV/msec, about 70 mV/msec, or about 75 mV/msec. In particular, the ramp rate can be from about 40 mV/msec to about 50 mV/msec.

In the DC component, the applied DC potential can be fixed at about 0 mV between pulses to provide a recovery pulse, thus making it a generally continuous excitation waveform. This is in contrast to test sequences generally known in the art that prescribe the use of an open circuit between positive DC pulses, thereby excluding the possibility of collecting and analyzing the current between positive pulses. As used herein, "recovery pulse" means a zero-potential pulse (e.g., about −10 mV to about +10 mV) applied for an adequately long recovery period in which the electrochemical reaction with the analyte of interested (e.g., glucose) is turned "off," thereby allowing the system to return to a fixed starting point before subsequent interrogation with another positive DC pulse.

An exemplary DC component therefore can alternate (i.e., pulse) between about 0 mV and about +450 mV (in biamperometric mode). Alternatively, an exemplary DC component can alternate between about −450 mV and about +450 mV.

Like the AC component, one of skill in the art understands that the number, potential, duration and order of the pulses in the DC component can be varied.

The responses to the test sequence are recorded and used to assess analyte concentration and/or presence in the body fluid sample. Important response information includes, but is not limited to, duration, shape and/or magnitude of the current response to an excitation pulse and/or a recovery pulse in the test sequence. Such information can be used not only to determine the analyte concentration but also to correct for interferents such as HCT and temperature but also wetting of the reagent and sample diffusion, as well as variations in detection reagent thickness.

Additional details regarding exemplary electrochemical measurement methods are disclosed in, for example, U.S. Pat. Nos. 4,008,448; 4,225,410; 4,233,029; 4,323,536; 4,891,319; 4,919,770; 4,963,814; 4,999,582; 4,999,632; 5,053,199; 5,108,564; 5,120,420; 5,122,244; 5,128,015; 5,243,516; 5,288,636; 5,352,351; 5,366,609; 5,385,846; 5,405,511; 5,413,690; 5,437,999; 5,438,271; 5,508,171; 5,526,111; 5,627,075; 5,628,890; 5,682,884; 5,727,548; 5,762,770; 5,858,691; 5,997,817; 6,004,441; 6,054,039; 6,254,736; 6,270,637; 6,645,368; 6,662,439; 7,073,246; 7,018,843; 7,018,848; 7,045,054; 7,115,362; 7,276,146; 7,276,147; 7,335,286; 7,338,639; 7,386,937; 7,390,667; 7,407,811; 7,429,865; 7,452,457; 7,488,601; 7,494,816; 7,545,148; 7,556,723; 7,569,126; 7,597,793; 7,638,033; 7,731,835; 7,751,864; 7,977,112; 7,981,363; 8,148,164; 8,298,828; 8,329,026; 8,377,707; and 8,420,404, as well as RE36268, RE42560, RE42924 and RE42953. Other exemplary electrochemical measurement methods that can be used herein are disclosed in Int'l Patent Application Publication Nos. WO 2014/140718; WO 2014/140164; WO 2014/140170; WO 2014/140172; WO 2014/140173; and WO 2014/140177.

The analyte concentrations can be determined by algorithms and/or correlations to the amount of redox equivalents (e.g., electrons) liberated or consumed in the detection reagents and measured via the electrode system, where such algorithms and/or correlations are known in the art.

Aside from the analyte measurement steps, the analyte measurement methods also can include the correcting/compensating steps described above. That is, the methods also can include determining $R_s$ of a biosensor in $\Omega$/square at a time of use by measuring resistance of one or more patterns of conductive elements in the form of, for example, conductive squares and then dividing by the theoretical number of uncompensated conductive squares in the pattern of conductive elements to obtain $R_{UNC}$, which subsequently can be used to correct for uncompensated resistances in the conductive elements.

Figure 15:
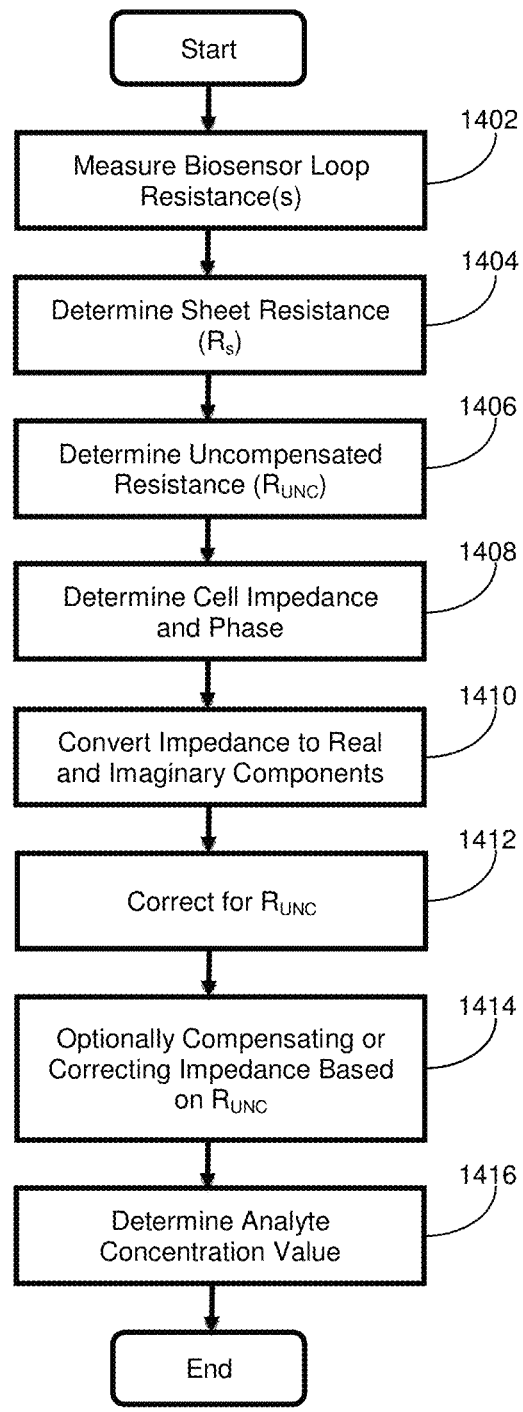
FIG. 15 is a flow chart setting forth steps for an exemplary method of operating a biosensor or test system in accordance with the present disclosure.

In some instances, and referring now to FIG. 15, the correcting/compensating steps may be carried out by a processor or controller or other components of a measurement device, as a non-limiting example, coupled to a biosensor, such as through the connection terminal (or biosensor port) as shown in FIG. 5.

The non-limiting process steps illustrated in FIG. 15 can begin at process component 1402 with measuring one or more loop resistances and, at process component 1404, determining $R_s$ of the conductive elements, such as:

$$R_s = \Omega/\#\text{squares} \qquad \text{Equation 15}$$

At process component 1406, the process includes determining an amount of $R_{UNC}$ included in a given cell (e.g., the CE or WE), such as:

$$R_{UNC} = R_s \times N(\text{conductive squares}),$$

where such conductive squares are those 'after,' 'beyond' or 'outside' that pattern or path of conductive elements used to determine $R_s$ Equation 16

The number of conductive squares in the WE and CE can be estimated, experimentally determined, theoretically identified, or simulated.

At process component 1408, the process includes determining cell impedance and phase using measured loop current, such as:

$$|Z|(\Omega)=V_1/I_{LOOP} \text{ and } \theta(°)=\sphericalangle I_{LOOP} \qquad \text{Equation 17}$$

At process component 1410, the process includes converting impedance into real and imaginary components, such as:

$$Z_{REAL}(\Omega)=|Z|\times\cos(\theta) \qquad \text{Equation 18}$$

$$Z_{IMAG}(\Omega)=|Z|\times\sin(\theta) \qquad \text{Equation 19}$$

At process component 1412, the process includes correcting for $R_{UNC}$, which can be achieved by correcting the real impedance by subtracting the $R_{UNC}$, such as:

$$Z'_{REAL}(\Omega)=Z_{REAL}(\Omega)-R_{UNC}(\Omega) \qquad \text{Equation 20}$$

At process component 1414, the process includes optionally converting the real and original imaginary components to corrected magnitude and phase, such as:

$$|Z'|(\Omega)=\sqrt{[(Z'_{REAL})^2]} \text{ and } \theta'(°)=-\tan^{-1}(Z_{IMAG}/Z'_{REAL}) \qquad \text{Equation 21}$$

At process component 1416, the process includes determining an analyte concentration value. In some instances, the original measurements are replaced with corrected Z' and θ'. At process component 1416, the process may be repeated if all evaluation criteria have not been considered. Some non-limiting criteria may include frequencies or temperature ranges (such as based on temperature readings from a thermistor included in the measurement device). That is, if the above-described steps have not been completed for each frequency or for a range of operating temperature, the process may be repeated.

EXAMPLES

The inventive concept will be more fully understood upon consideration of the following non-limiting examples, which are offered for purposes of illustration, not limitation.

Example 1

Figure 16:
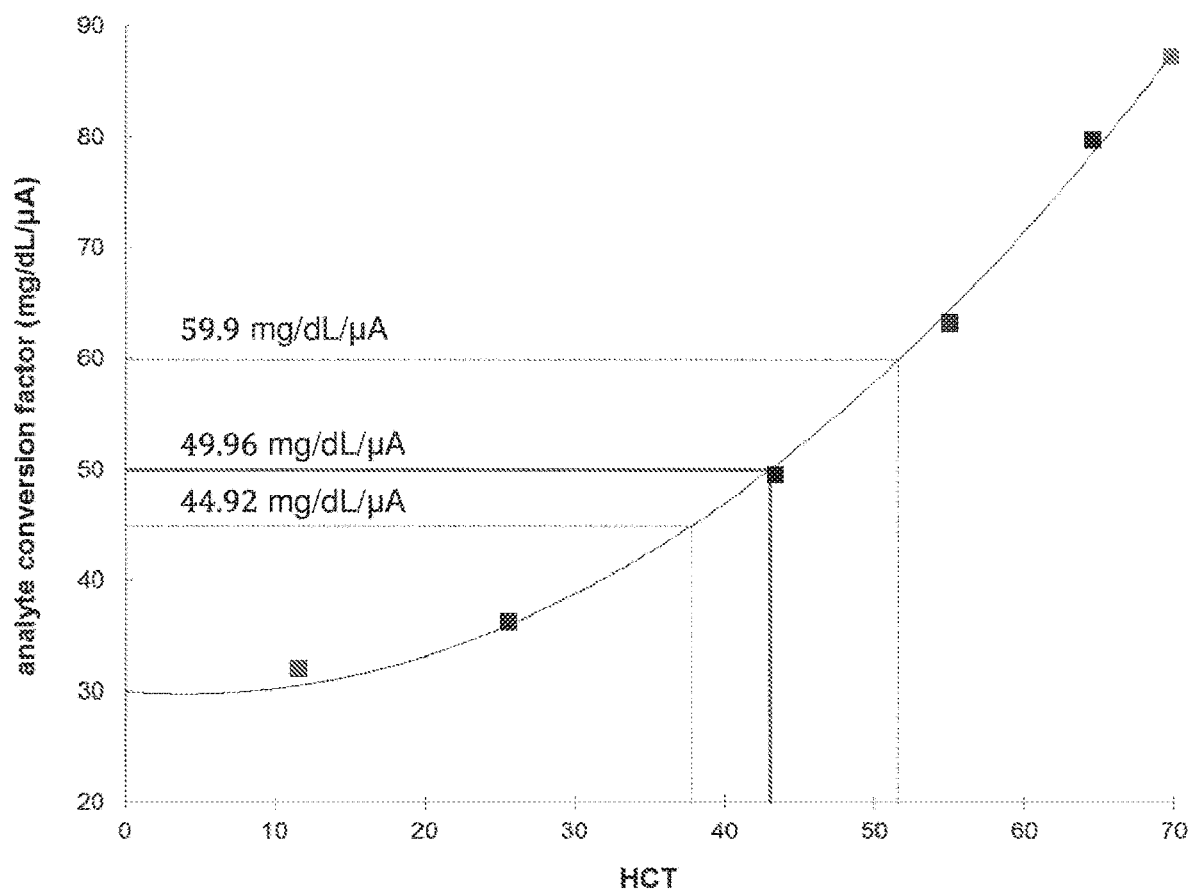
FIG. 16 is a graph showing operational results performed using a biosensor to analyze glucose as a function of perceived hematocrit (HCT; 11.6%, 25.6%, 43.4%, 55.0%, 64.6%, 69.8%) based on a low $R_s$ (3.8 Ω/square) and high $R_s$ (4.75 Ω/square) versus a nominal $R_s$ (4.21 Ω/square).

FIG. 16 shows one example for evaluating operational results from electrochemical biosensors used to analyze a fixed glucose concentration in the presence of varying HCT (e.g., 11.6%, 25.6, 43.4%, 55.0%, 64.6% and 69.8%). Specifically, FIG. 16 shows average data from a blood sample and a biosensor having hybrid metal conductive elements with a $R_s$ of 4.2 Ω/square. FIG. 16 therefore shows a demonstrated sensitivity change, which becomes more significant as sample conductivity decreases (lower HCT).

Figure 17:
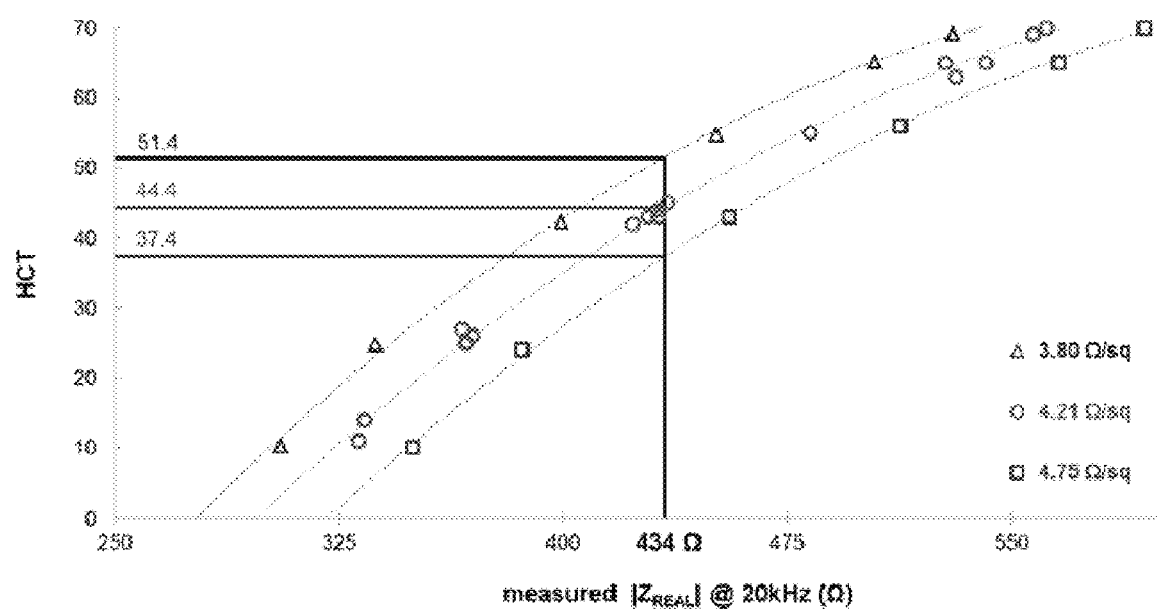
FIG. 17 shows one example for converting R (or $Z_{REAL}$) to HCT that can be used in connection with FIG. 16. The low $R_s$ in Ω/square is represented by triangles (▲), the nominal $R_s$ in Ω/square is represented by circles (●), and the high $R_s$ in Ω/square is resented by squares (■).

More specifically, in this example, an experiment was performed to measure a DC response of 2 μA and a high frequency impedance with a real portion of 434Ω. With no $R_{UNC}$ correction, and as shown in FIG. 17, $Z_{REAL}$ was directly converted to a 44.4 HCT based on a nominal resistivity. The correct calibration curve was selected (49.96 mg/dL/ρA) as shown in FIG. 16, and the measured 2 μA current correctly converted to 99.9 mg/dL (e.g., 49.96 mg/dL/μA×2 μA=99.92 mg/dL).

If the resistivity of the biosensor base material is higher than nominal (e.g., 4.75 Ω/square), an uncorrected 434Ω $Z_{REAL}$ measurement would be converted to HCT=37.4. An incorrect calibration curve would be selected (44.92 mg/dL/μA) from FIG. 16, and the measured 2 μA current converted to 89.8 mg/dL (−10% error; e.g., 44.92 mg/dL/μA×2 μA=89.84 mg/dL). FIG. 17 shows one example for converting R (or $Z_{REAL}$) to HCT that can be used in connection with the data shown in FIG. 16.

On the other hand, if the resistivity of the biosensor base material is 10% lower than nominal (e.g., 3.80 Ω/square), an uncorrected 434Ω $Z_{REAL}$ would be converted to HCT=51.6. An incorrect calibration curve would be selected (59.9 mg/dL/μA), and the measured 2 μA current converted to ≈119.8 mg/dL (+20% error; e.g., 59.9 mg/dL/μA×2 μA=119.8 mg/dL). Thus, it can be seen that the above-described systems and methods for selecting proper calibration yields a substantial improvement in the ultimate analysis accuracy of the biosensor or test strip.

To further illustrate the effectiveness of the methods herein, four additional studies were conducted, where $R_s$ was varied from 0.2, 3.8, 4.2, and 4.8 Ω/square, respectively. Table 1 shows results from an electrode made with a conductive material of reasonable thickness, where the $R_s$ was about 0.2 Ω/square. If the electrodes have a low $R_s$, then there essentially is no significant $R_{UNC}$ to be corrected. The electrode design has about sixteen (16) squares for the $R_{UNC}$ region; therefore, $R_{UNC}=16\times0.2$ Ω/square=3.6Ω not much of a correction when the mean 20 kHz $|Z_{REAL}|$ is from about 249.8Ω to about 474.6Ω. So the $Z_{REAL}$ corrected glucose (mg/dL) is akin to a value uncorrected for $R_{UNC}$. $Z_{REAL}$ therefore is the value that is obtained from the AC component in the exemplary measurement method and is the measured value that would have contributions from both HCT and $R_{UNC}$. In this case even if the value is corrected for $R_{UNC}$, the difference is small because $R_{UNC}$ is small.

TABLE 1

$R_{UNC}$ Contribution to Concentration Error (near-ideal $R_s = 0.2$ Ω/square; glucose reference = 120 mg/dL)

| HCT | Mean 20 kHz $|Z_{REAL}|$ | $Z_{REAL}$ Corrected Glucose (mg/dL) | $Z_{REAL}$ Corrected Glucose Error | $R_{UNC}$ Corrected Glucose (mg/dL) | $R_{UNC}$ Corrected Glucose Error |
|---|---|---|---|---|---|
| 11.6 | 249.8 Ω | 121.7 | 1.4% | 121.4 | 1.2% |
| 25.6 | 282.7 Ω | 121.7 | 1.4% | 121.6 | 1.4% |
| 43.4 | 343.8 Ω | 118.8 | −1.0% | 118.7 | −1.1% |
| 55.0 | 395.4 Ω | 117.8 | −1.8% | 117.8 | −1.8% |
| 64.6 | 445.0 Ω | 119.1 | −0.8% | 119.1 | −0.8% |
| 69.8 | 474.6 Ω | 118.9 | −0.9% | 118.9 | −0.9% |

In contrast, Tables 2-4 show results with gradually increasing $R_s$ values. Here, the test strips have a less conductive thin film electrode and thus are more resistive when compared to test strips from Table 1, which shows how correcting for $R_{UNC}$ can improve the calculated glucose. This is about a range that would be seen with normal manufacturing methods.

TABLE 2

$R_{UNC}$ Contribution to Concentration Error (low $R_s = 3.8$ Ω/square; glucose reference = 120 mg/dL)

| HCT | Mean 20 kHz $|Z_{REAL}|$ | $Z_{REAL}$ Corrected Glucose (mg/dL) | $Z_{REAL}$ Corrected Glucose Error | $R_{UNC}$ Corrected Glucose (mg/dL) | $R_{UNC}$ Corrected Glucose Error |
|---|---|---|---|---|---|
| 11.6 | 307.4 Ω | 147.5 | +23% | 122.2 | 1.8% |
| 25.6 | 340.3 Ω | 149.2 | +24% | 121.9 | 1.5% |
| 43.4 | 401.4 Ω | 146.7 | +22% | 118.5 | −1.2% |

TABLE 2-continued $R_{UNC}$ Contribution to Concentration Error (low $R_s$ = 3.8 Ω/square; glucose reference = 120 mg/dL)

| HCT | Mean 20 kHz $|Z_{REAL}|$ | $Z_{REAL}$ Corrected Glucose (mg/dL) | $Z_{REAL}$ Corrected Glucose Error | $R_{UNC}$ Corrected Glucose (mg/dL) | $R_{UNC}$ Corrected Glucose Error |
|---|---|---|---|---|---|
| 55.0 | 453.0 Ω | 145.2 | +21% | 117.4 | −2.1% |
| 64.6 | 502.6 Ω | 145.7 | +21% | 118.5 | −1.2% |
| 69.8 | 532.2 Ω | 144.8 | +21% | 118.3 | −1.4% |

TABLE 3

$R_{UNC}$ Contribution to Concentration Error (nominal $R_s$ = 4.2 Ω/square; glucose reference = 120 mg/dL)

| HCT | Mean 20 kHz $|Z_{REAL}|$ | $Z_{REAL}$ Corrected Glucose (mg/dL) | $Z_{REAL}$ Corrected Glucose Error | $R_{UNC}$ Corrected Glucose (mg/dL) | $R_{UNC}$ Corrected Glucose Error |
|---|---|---|---|---|---|
| 11.6 | 313.8 Ω | 150.9 | +26% | 120.5 | 0.4% |
| 25.6 | 346.7 Ω | 152.7 | +27% | 120.4 | 0.3% |
| 43.4 | 407.8 Ω | 150.2 | +25% | 117.4 | −2.2% |
| 55.0 | 459.4 Ω | 148.5 | +24% | 116.5 | −2.9% |
| 64.6 | 509.0 Ω | 148.9 | +24% | 117.7 | −1.9% |
| 69.8 | 538.6 Ω | 147.9 | +23% | 117.6 | −2.0% |

TABLE 4

$R_{UNC}$ Contribution to Concentration Error (high $R_s$ = 4.8 Ω/square; glucose reference = 120 mg/dL)

| HCT | Mean 20 kHz $|Z_{REAL}|$ | $Z_{REAL}$ Corrected Glucose (mg/dL) | $Z_{REAL}$ Corrected Glucose Error | $R_{UNC}$ Corrected Glucose (mg/dL) | $R_{UNC}$ Corrected Glucose Error |
|---|---|---|---|---|---|
| 11.6 | 323.4 Ω | 156.2 | +30% | 120.5 | 0.4% |
| 25.6 | 356.3 Ω | 158.2 | +32% | 120.4 | 0.3% |
| 43.4 | 417.4 Ω | 155.5 | +30% | 117.4 | −2.2% |
| 55.0 | 469.0 Ω | 153.6 | +28% | 116.5 | −2.9% |
| 64.6 | 518.6 Ω | 153.8 | +28% | 117.7 | −1.9% |
| 69.8 | 548.2 Ω | 152.6 | +27% | 117.6 | −2.0% |

As these tables show, at each HCT examined, the greater the $R_s$, the greater the glucose error. The compensation methods described herein, however, were able to correct the glucose error to within ±3% of the target glucose value of 120 mg/dL over the range of HCTs.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims. Numbered embodiments are presented below.

Numbered Embodiments

In addition or as an alternative to the above, the following embodiments are described:

1. A method of compensating, correcting or minimizing uncompensated resistances in a biosensor for use in determining an analyte concentration, the method comprising the steps of:
   applying a potential difference to the biosensor, wherein the biosensor comprises:
      a number of conductive elements including at least a working electrode, a working electrode voltage-sensing trace, a counter electrode, and a counter electrode voltage-sensing trace; and
      a detection reagent contacting one or more of the conductive elements;
   wherein the potential difference is applied between the working electrode and the counter electrode and each of the working electrode and the counter electrode is segmentable into an uncompensated connecting portion and an uncompensated active portion, wherein the uncompensated connecting portions begin after connection of each of the respective voltage-sensing traces to the working electrode and the counter electrode, and wherein each uncompensated connecting portion and uncompensated active portion is further segmentable into a number of conductive squares;
   determining sheet resistances for the working electrode and the counter electrode based upon the applied potential difference by measuring resistances of one or more compensation loops formed by the working electrode, the counter electrode, and the voltage-sensing traces, dividing each resistance of the one or more compensation loops by a predetermined number of squares in the compensation loop, and mathematically combining the results to determine the sheet resistance representative of the conductive elements;
   determining uncompensated resistances for the working electrode and the counter electrode based upon the sheet resistances and the number of conductive squares; and
   mathematically compensating or correcting impedance based upon the determined uncompensated resistances.
2. The method of embodiment 1, wherein the potential comprises at least one alternating current (AC) component.
3. The method of embodiment 2, wherein the at least one AC component comprises frequencies of about 10 kHz, about 20 kHz, about 10 kHz, about 2 kHz and about 1 kHz, and wherein each frequency is applied for about 0.5 seconds to about 1.5 seconds.
4. The method of embodiment 2, wherein the at least one AC component comprises frequencies of about 20 kHz, about 10 kHz, about 2 kHz and about 1 kHz, and wherein each frequency is applied for about 0.5 seconds to about 1.5 seconds.
5. The method of embodiment 2, wherein the potential further comprises at least one direct current (DC) component.
6. The method of embodiment 5, wherein the at least one DC component comprises a plurality of potential pulses ramped to or from about 0 V to about +450 mV with each pulse being separated by a recovery interval during which about a 0 mV potential difference is applied between the counter electrode and the working electrode.

7. The method of embodiment 5, wherein the at least one DC component comprises a plurality of potential pulses that alternates between about −450 mV to about +450 mV.
8. The method of embodiment 1, further comprising the step of determining an analyte concentration in a body fluid sample having or suspected of having an analyte of interest, wherein the body fluid is in fluidic contact with the detection reagent.
9. A method of electrochemically measuring concentration or presence of an analyte of interest in a body fluid sample, the method comprising the steps of:
 applying the body fluid sample to a biosensor, wherein the biosensor comprises:
  a non-conductive base supporting conductive elements of a working electrode in the biosensor;
  a number of conductive elements including at least one or more of a working electrode, a working electrode trace, a working electrode contact pad, a working electrode voltage-sensing trace, and a counter electrode; and
  a detection reagent contacting one or more of the conductive elements;
  wherein the conductive elements are arranged as a compensation loop and an uncompensated portion, the uncompensated portion further comprising an uncompensated connecting portion and an uncompensated active portion, wherein the uncompensated portions begin after connection of the working electrode voltage-sensing trace to the working electrode, and wherein each of the compensation loop, the uncompensated connecting portion and the uncompensated active portion is segmentable into a plurality of conductive squares;
 applying a potential difference to the biosensor;
 determining a sheet resistance for one or more conductive squares in the plurality of conductive squares based on a measurement of a resistance generated through the compensation loop in response to the potential difference and a predetermined first number of the plurality of conductive squares in the compensation loop;
 determining an uncompensated resistance for the working electrode based upon the sheet resistance of the one or more conductive squares and a predetermined second number of the plurality of conductive squares in the uncompensated portion;
 applying an electrical test sequence to the working electrode and the counter electrode of the biosensor and measuring response information thereto, wherein the electrical test sequence includes at least one AC component and at least one DC component;
 mathematically compensating or correcting impedance based upon the uncompensated resistance; and
 determining one or more analyte concentrations with the test meter using the response information to the test sequence and based upon DC component and the mathematically compensated or corrected impedance.
10. The method of embodiment 9, wherein the at least one AC component comprises frequencies of about 10 kHz, about 20 kHz, about 10 kHz, about 2 kHz and about 1 kHz, and wherein each frequency is applied for about 0.5 seconds to about 1.5 seconds.
11. The method of embodiment 9, wherein the at least one AC component comprises frequencies of about 20 kHz, about 10 kHz, about 2 kHz and about 1 kHz, and wherein each frequency is applied for about 0.5 seconds to about 1.5 seconds.
12. The method of embodiment 9, wherein the at least one DC component comprises a plurality of potential pulses ramped to or from about 0 V to about +450 mV with each pulse being separated by a recovery interval during which about a 0 mV potential difference is applied between the counter electrode and the working electrode.
13. The method of embodiment 9, wherein the at least one DC component comprises a plurality of potential pulses that alternates between about −450 mV to about +450 mV.
14. The method of embodiment 9, wherein the analyte of interest is glucose.
15. A method of increasing biosensor computation accuracy and reliability, the method comprising the steps of:
 providing a biosensor, wherein the biosensor comprises:
  a non-conductive base supporting conductive elements of a working electrode in the biosensor;
  a number of conductive elements including at least one or more of a working electrode, a working electrode trace, a working electrode contact pad, a working electrode voltage-sensing trace, a working electrode voltage-sensing contact pad, and a counter electrode; and
  a detection reagent contacting one or more of the conductive elements,
  wherein the conductive elements are arranged as a compensation loop and an uncompensated portion, the uncompensated portion further comprising an uncompensated connecting portion and an uncompensated active portion, wherein the uncompensated portion begins after connection of any voltage-sensing trace to the working electrode, and wherein each of the compensation loop, the uncompensated connecting portion and the uncompensated active portion is further segmentable into a plurality of conductive squares;
 applying a potential difference to the biosensor;
 determining a sheet resistance for one or more conductive squares in the plurality of conductive squares based on a measurement of a resistance generated through the compensation loop in response to the potential difference and a predetermined first number of the plurality of conductive squares in the compensation loop;
 determining an uncompensated resistance for the working electrode based upon the sheet resistance for the one or more conductive squares and a predetermined second number of the number of conductive squares in the uncompensated portion; and
 mathematically compensating or correcting impedance by subtracting the uncompensated resistance from a real portion of a measured impedance.
16. The method of embodiment 15, wherein the potential comprises at least one alternating current (AC) component.
17. The method of embodiment 16, wherein the at least one AC component comprises frequencies of about 10 kHz, about 20 kHz, about 10 kHz, about 2 kHz and about 1 kHz, and wherein each frequency is applied for about 0.5 seconds to about 1.5 seconds.
18. The method of embodiment 16, wherein the at least one AC component comprises frequencies of about 20 kHz, about 10 kHz, about 2 kHz and about 1 kHz, and wherein each frequency is applied for about 0.5 seconds to about 1.5 seconds.

19. A device configured to perform the method of embodiment 1.

20. The device of embodiment 19, wherein the device is a blood glucose meter.

21. A system comprising the device of embodiment 19 and at least one biosensor.

22. The system of embodiment 21, wherein the system is a self-monitoring blood glucose (SMBG) system.

23. A device configured to perform the method of embodiment 9.

24. The device of embodiment 23, wherein the device is a blood glucose meter.

25. A system comprising the device of embodiment 23 and at least one biosensor.

26. The system of embodiment 25, wherein the system is a self-monitoring blood glucose (SMBG) system.

27. A device configured to perform the method of embodiment 15.

28. The device of embodiment 27, wherein the device is a blood glucose meter.

29. A system comprising the device of embodiment 27 and at least one biosensor.

30. The system of embodiment 29, wherein the system is a self-monitoring blood glucose (SMBG) system.

LISTING OF REFERENCE NUMBERS

| | |
|---|---|
| 10 | biosensor |
| 12 | support substrate |
| 14 | spacer |
| 16 | cover |
| 18 | first surface |
| 20 | second surface |
| 22 | end |
| 24 | end |
| 26 | side edge |
| 28 | side edge |
| 30 | capillary channel |
| 32 | end edge |
| 34 | inner surface |
| 36 | lower surface |
| 40 | connection terminal |
| 42 | display |
| 44 | entry means |
| 100 | biosensor |
| 102 | measurement device |
| 102a | measuring circuit |
| 104 | working electrode (WE) |
| 106 | counter electrode (CE) |
| 108 | CE trace |
| 110 | WE trace |
| 112 | WE voltage-sensing trace |
| 114 | sample receiving chamber |
| 116 | CE flow |
| 118 | Point "B" |
| 120 | Point "A" |
| 122 | WE flow |
| 124 | CE voltage-sensing trace |
| 200 | biosensor |
| 300 | biosensor |
| 600 | biosensor |
| 602 | WE voltage-sensing trace |
| 604 | CE voltage-sensing trace |
| 606 | WE trace |
| 608 | CE trace |
| 610 | WE |
| 612 | CE |

-continued

| | |
|---|---|
| 614 | reaction zone |
| 616 | WE uncompensated connecting portion |
| 618 | CE uncompensated connecting portion |
| 620 | WE uncompensated active portion |
| 622 | CE uncompensated active portion |
| 624 | WE end |
| 626 | CE end |
| 700 | measuring circuit |
| 702 | first resistor |
| 704 | second resistor |
| 706 | load resistor |
| 802 | WE conductive squares |
| 802a-c | WE uncompensated connecting portion conductive squares |
| 802d-k | WE uncompensated active portion conductive squares |
| 802l | WE end conductive square |
| 804 | CE conductive squares |
| 804a-c | CE uncompensated connecting portion conductive squares |
| 804d-k | CE uncompensated active portion conductive squares |
| 804l | CE end conductive square |
| 1402 | Calculating step (cell impedance and phase) |
| 1404 | Converting step |
| 1406 | Measuring step |
| 1408 | Calculating step (sheet resistance) |
| 1410 | Calculating step (uncompensated resistance) |
| 1412 | Correcting step |
| 1414 | Converting step |
| 1416 | Evaluating step |

What is claimed is:

1. A method of compensating, correcting or minimizing uncompensated resistances in a biosensor for use in determining an analyte concentration, comprising:
    measuring, with a measuring circuit in a measuring device, an electrical resistance of a compensation loop formed in a first electrode or a second electrode of the biosensor that is electrically connected to the measuring circuit;
    identifying, with the measuring circuit and a processor in the measuring device, a sheet resistance value for a square region having a predetermined size within the compensation loop based on the electrical resistance and a ratio between the predetermined size of the square region and a predetermined total size of the compensation loop;
    identifying, with the processor, an uncompensated electrical resistance value of the first electrode based on the sheet resistance value of the square region, a first predetermined plurality of the square regions that correspond to a connecting portion of the first electrode, and a second predetermined plurality of the square regions that correspond to an active portion of the first electrode, wherein the connecting portion and the active portion of the first electrode are located outside of the compensation loop;
    applying, with the measuring circuit, an electrical test sequence to the first electrode and the second electrode after a fluid sample is applied to a reagent that contacts the active portion of the first electrode; and
    identifying, with the measuring circuit and the processor, a level of an analyte in the fluid sample based at least in part on responses received from the electrical test sequence and a corrected impedance value corresponding to an impedance between the first electrode and the second electrode, wherein the processor generates the corrected impedance value based on a subtraction of the uncompensated electrical resistance of the first electrode from a real component of a measured impedance value between the first electrode and the second electrode.

2. The method of claim 1, wherein identifying of the uncompensated electrical resistance value of the first electrode further comprises:
identifying, with the processor, the uncompensated electrical resistance value of the first electrode based on the sheet resistance value of the square region multiplied by a sum of the first predetermined plurality of the square regions that correspond to the connecting portion of the first electrode and a quotient of the second predetermined plurality of the square regions that correspond to the active portion of the first electrode divided by a predetermined divisor.

3. The method of claim 2, wherein the predetermined divisor is 2.

4. The method of claim 1, further comprising:
identifying, with the processor, an uncompensated electrical resistance value of the second electrode based on the sheet resistance value of the square region, a third predetermined plurality of the square regions that correspond to a connecting portion of the second electrode, and a fourth predetermined plurality of the square regions that correspond to an active portion of the second electrode, wherein the connecting portion and the active portion of the second electrode are located outside of the compensation loop; and
subtracting with the processor the uncompensated electrical resistance of the second electrode from the real component of the measured impedance value between the first electrode and the second electrode to generate the corrected impedance value during the identifying of the level of the analyte.

5. The method of claim 4, wherein identifying of the uncompensated electrical resistance value of the second electrode further comprises:
identifying, with the measuring circuit, an uncompensated electrical resistance value of the second electrode based on the sheet resistance value of the square region multiplied by a sum of the third predetermined plurality of the square regions that correspond to the connecting portion of the second electrode and a quotient of the fourth predetermined plurality of the square regions that correspond to the active portion of the second electrode divided by a predetermined divisor.

6. The method of claim 5, wherein the predetermined divisor is 2.

7. The method of claim 1, wherein the identifying of the level of the analyte further comprises:
selecting, with the processor, a calibration curve from a plurality of calibration curves based on the corrected impedance value; and
identifying, with the processor, the level of the analyte using the selected calibration curve.

8. The method of claim 1, wherein the first electrode is a working electrode and the second electrode is a counter electrode.

9. The method of claim 1, wherein the first electrode is a counter electrode and the second electrode is a working electrode.

10. The method of claim 1, wherein the electrical test sequence includes at least one AC component and at least one DC component.

11. The method of claim 10, wherein the at least one AC component comprises frequencies of about 10 kHz, about 20 kHz, about 10 kHz, about 2 kHz and about 1 kHz, and wherein each frequency is applied for about 0.5 seconds to about 1.5 seconds.

12. The method of claim 10, wherein the at least one AC component comprises frequencies of about 20 kHz, about 10 kHz, about 2 kHz and about 1 kHz, and wherein each frequency is applied for about 0.5 seconds to about 1.5 seconds.

13. The method of claim 10, wherein the at least one DC component comprises a plurality of potential pulses ramped to or from about 0 V to about +450 mV with each pulse being separated by a recovery interval during which about a 0 mV potential difference is applied between the first electrode and the second electrode.

14. The method of claim 10, wherein the at least one DC component comprises a plurality of potential pulses that alternate between about −450 mV to about +450 mV.

15. The method of claim 1, wherein the analyte is glucose.

16. A blood glucose meter, comprising a measuring circuit, a processor, and a biosensor port configured to receive a biosensor, wherein:
the measuring circuit is configured to measure an electrical resistance of a compensation loop formed in a first electrode or a second electrode of the biosensor when the biosensor is received in the biosensor port and is electrically connected to the measuring circuit;
the measuring circuit and the processor are configured to identify a sheet resistance value for a square region having a predetermined size within the compensation loop based on the electrical resistance and a ratio between the predetermined size of the square region and a predetermined total size of the compensation loop;
the processor is further configured to identify an uncompensated electrical resistance value of the first electrode based on the sheet resistance value of the square region, a first predetermined plurality of the square regions that correspond to a connecting portion of the first electrode, and a second predetermined plurality of the square regions that correspond to an active portion of the first electrode, wherein the connecting portion and the active portion of the first electrode are located outside of the compensation loop;
the measuring circuit is configured to apply an electrical test sequence to the first electrode and the second electrode after a fluid sample is applied to a reagent that contacts the active portion of the first electrode; and
the measuring circuit and the processor are further configured to identify a level of an analyte in the fluid sample based at least in part on responses received from the electrical test sequence and a corrected impedance value corresponding to an impedance between the first electrode and the second electrode, wherein the processor generates the corrected impedance value based on a subtraction of the uncompensated electrical resistance of the first electrode from a real component of a measured impedance value between the first electrode and the second electrode.

17. The blood glucose meter of claim 16, wherein the processor is further configured to identify the uncompensated electrical resistance value of the first electrode based on the sheet resistance value of the square region multiplied by a sum of the first predetermined plurality of the square regions that correspond to the connecting portion of the first electrode and a quotient of the second predetermined plurality of the square regions that correspond to the active portion of the first electrode divided by a predetermined divisor.

18. The blood glucose meter of claim 17, wherein the predetermined divisor is 2.

19. The blood glucose meter of claim 16, wherein the processor is further configured to:
   identify an uncompensated electrical resistance value of the second electrode based on the sheet resistance value of the square region, a third predetermined plurality of the square regions that correspond to a connecting portion of the second electrode, and a fourth predetermined plurality of the square regions that correspond to an active portion of the second electrode, wherein the connecting portion and the active portion of the second electrode are located outside of the compensation loop; and
   subtract the uncompensated electrical resistance of the second electrode from the real component of the measured impedance value between the first electrode and the second electrode to generate the corrected impedance value during the identifying of the level of the analyte.

20. The blood glucose meter of claim 19, wherein the measuring circuit is further configured to identify an uncompensated electrical resistance value of the second electrode based on the sheet resistance value of the square region multiplied by a sum of the third predetermined plurality of the square regions that correspond to the connecting portion of the second electrode and a quotient of the fourth predetermined plurality of the square regions that correspond to the active portion of the second electrode divided by a predetermined divisor.

21. The blood glucose meter of claim 20, wherein the predetermined divisor is 2.

22. The blood glucose meter of claim 16, wherein the processor is further configured to select a calibration curve from a plurality of calibration curves based on the corrected impedance value and to identify the level of the analyte using the selected calibration curve.

23. The blood glucose meter of claim 16, wherein the first electrode is a working electrode and the second electrode is a counter electrode.

24. The blood glucose meter of claim 16, wherein the first electrode is a counter electrode and the second electrode is a working electrode.

25. The blood glucose meter of claim 16, wherein the electrical test sequence includes at least one AC component and at least one DC component.

26. The blood glucose meter of claim 25, wherein the at least one AC component comprises frequencies of about 10 kHz, about 20 kHz, about 10 kHz, about 2 kHz and about 1 kHz, and wherein each frequency is applied for about 0.5 seconds to about 1.5 seconds.

27. The blood glucose meter of claim 25, wherein the at least one AC component comprises frequencies of about 20 kHz, about 10 kHz, about 2 kHz and about 1 kHz, and wherein each frequency is applied for about 0.5 seconds to about 1.5 seconds.

28. The blood glucose meter of claim 25, wherein the at least one DC component comprises a plurality of potential pulses ramped to or from about 0 V to about +450 mV with each pulse being separated by a recovery interval during which about a 0 mV potential difference is applied between the first electrode and the second electrode.

29. The blood glucose meter of claim 25, wherein the at least one DC component comprises a plurality of potential pulses that alternate between about −450 mV to about +450 mV.

30. The blood glucose meter of claim 16, wherein the analyte is glucose.

* * * * *